(12) United States Patent
Orth et al.

(10) Patent No.: US 12,016,774 B2
(45) Date of Patent: Jun. 25, 2024

(54) DELIVERY SYSTEM FOR PROSTHETIC VALVE DEVICE HAVING CONTROLLED RELEASE OF INFLOW AND OUTFLOW ENDS

(71) Applicant: MEDTRONIC VASCULAR, INC., Santa Rosa, CA (US)

(72) Inventors: Geoffrey Orth, Sebastopol, CA (US); Edmond Sheahan, Knocknacarra (IE); Lawrence D. Jones, Westford, MA (US); Laura Ruddy, Mayo (IE); Huda Khilji, Virginia (IE); Cathleen A. Bergin, Hugo, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 327 days.

(21) Appl. No.: 17/306,039

(22) Filed: May 3, 2021

(65) Prior Publication Data

US 2021/0346158 A1 Nov. 11, 2021

Related U.S. Application Data

(60) Provisional application No. 63/022,016, filed on May 8, 2020.

(51) Int. Cl.
  *A61F 2/24* (2006.01)
  *A61F 2/966* (2013.01)
  *A61F 2/95* (2013.01)

(52) U.S. Cl.
  CPC .......... *A61F 2/2436* (2013.01); *A61F 2/2418* (2013.01); *A61F 2002/9665* (2013.01)

(58) Field of Classification Search
  CPC ...... A61F 2/2436; A61F 2/2418; A61F 2/966; A61F 2/2427; A61F 2/24; A61F 2/2412; A61F 2002/9665
  See application file for complete search history.

(56) References Cited

U.S. PATENT DOCUMENTS 5,234,437 A  8/1993  Sepetka
5,480,424 A  1/1996  Cox
(Continued)

FOREIGN PATENT DOCUMENTS

EP  2 674 135 A1  12/2013
WO  2004110521 A2  12/2004
WO  2019195336 A1  10/2019

OTHER PUBLICATIONS

International Search Report and Written Opinion dated Aug. 25, 2021 in International Search Application No. PCT/US2021/031219.
(Continued)

*Primary Examiner* — Kelly J Bekker
*Assistant Examiner* — Lindsey R. Rivers
(74) *Attorney, Agent, or Firm* — MEDLER FERRO WOODHOUSE & MILLS PLLC

(57) ABSTRACT

A delivery system for a prosthetic valve device includes a first shaft including an outflow capture device mounted on a distal end thereof, a second shaft slidingly disposed over the first shaft and including an inflow capture device mounted on a distal end thereof, and a retractable sheath slidingly disposed over the second shaft to hold the prosthetic valve device in a radially compressed configuration for delivery to a body lumen. The inflow capture device is configured for releasable engagement through openings in a plurality of first attachment members on the device. The outflow capture device is configured for releasable engagement through openings in a plurality of second attachment members on the device.

19 Claims, 17 Drawing Sheets

(56) References Cited

U.S. PATENT DOCUMENTS

| | | | |
|---|---|---|---|
| 5,713,948 | A | 2/1998 | Uflacker |
| 5,797,952 | A | 8/1998 | Klein |
| 6,395,017 | B1 | 5/2002 | Dwyer et al. |
| 6,719,789 | B2 | 4/2004 | Cox |
| 7,942,924 | B1 | 5/2011 | Perez et al. |
| 8,337,541 | B2 | 12/2012 | Quadri et al. |
| 8,801,776 | B2 | 8/2014 | House et al. |
| 9,364,324 | B2 | 6/2016 | Rafiee et al. |
| 9,364,432 | B2 | 6/2016 | MacDonald et al. |
| 2003/0199963 | A1 | 10/2003 | Tower et al. |
| 2003/0199971 | A1 | 10/2003 | Tower et al. |
| 2004/0078071 | A1 | 4/2004 | Escamilla et al. |
| 2004/0147939 | A1 | 7/2004 | Rabkin et al. |
| 2004/0193209 | A1 | 9/2004 | Pavcnik et al. |
| 2005/0137693 | A1 | 6/2005 | Haug et al. |
| 2005/0137701 | A1 | 6/2005 | Salahieh et al. |
| 2006/0111771 | A1 | 5/2006 | Ton et al. |
| 2006/0155357 | A1 | 7/2006 | Melsheimer |
| 2006/0271149 | A1* | 11/2006 | Berez ............... A61B 17/12118 623/1.11 |
| 2007/0100414 | A1 | 5/2007 | Licata et al. |
| 2007/0100415 | A1 | 5/2007 | Licata et al. |
| 2008/0183272 | A1 | 7/2008 | Wood et al. |
| 2009/0306761 | A1* | 12/2009 | Hebert ...................... A61F 2/95 623/1.12 |
| 2011/0251664 | A1 | 10/2011 | Acosta De Acevedo |
| 2014/0277345 | A1 | 9/2014 | Havel et al. |
| 2015/0134054 | A1 | 5/2015 | Morrissey |

OTHER PUBLICATIONS

Bonhoeffer et al., "Percutaneous Insertion of the Pulmonary Valve," Journal of the American College of Cardiology 2002; 39: 1664-1669.

Bonhoeffer et al., "Transcatheter Implantation of a Bovine Valve in Pulmonary Position," Circulation 2000: 102: 813-816.

Khambadkone et al., "Percutaneous Pulmonary Valve Implantation in Humans," Circulation 1189-1197; Aug. 23, 2005.

* cited by examiner

DELIVERY SYSTEM FOR PROSTHETIC VALVE DEVICE HAVING CONTROLLED RELEASE OF INFLOW AND OUTFLOW ENDS

CROSS-REFERENCE TO RELATED APPLICATIONS

This application claims the benefit of U.S. Provisional Patent Application Ser. No. 63/022,016, filed May 8, 2020, which is hereby incorporated by reference in its entirety for all purposes.

FIELD OF THE INVENTION

The present invention relates generally to the treatment of cardiac valve disease using prosthetic valves, and more particularly to a delivery system for a prosthetic valve device configured to replace a malfunctioning pulmonary valve.

BACKGROUND

Natural heart valves, such as aortic valves, mitral valves, pulmonary valves and tricuspid valves, often become damaged by disease in such a manner that they fail to maintain blood flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement generally has been accomplished by major open heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, co-existing infection, or other physical limitations.

Recently, there has been increasing interest in minimally invasive and percutaneous replacement of cardiac valves, typically by way of catheterization. In minimally invasive procedures, a catheter is used to insert a mechanical or bioprosthetic valve in a lumen of a blood vessel via percutaneous entry through a distal blood vessel. In the specific context of pulmonary valve replacement, U.S. Patent Application Publication Nos. 2003/0199971 A1 and 2003/0199963 A1, both filed by Tower et al. and incorporated herein by reference, describe replacing a pulmonary valve with a venous valvular replacement. The replacement pulmonary valve is mounted on a balloon catheter and delivered percutaneously via the vascular system to the location of the failed pulmonary valve and expanded by the balloon to compress the native valve leaflets against the right ventricular outflow tract, anchoring and sealing the replacement valve.

Pulmonary valve replacement using venous valves is not available to all who might benefit from it due to the relatively narrow size range of available valved segments of veins, for example, with typical sizes available only up to a diameter of about 22 mm. The same limited availability of sizes also applied to pericardial valves. Unfortunately, many patients requiring pulmonary valve replacement are adults and children who have right ventricular outflow tracts that are larger than 22 mm in diameter. This could have resulted, for example, from having previously undergone transannular patch repair of tetralogy of Fallot during infancy. There are other causes, however, for an enlarged right ventricular outflow tract. Thus, venous valvular replacements with a limit of 22 mm diameters, cannot typically be securely implanted within these patients. The same generally applies for pericardial heart valve replacements.

Thus, there is a continuing need to improve upon the devices available for heart valve replacement. In addition, there is a continuing need for improved transcatheter delivery systems and methods of implanting medical devices, and particularly systems related to heart valve replacement.

SUMMARY

According to a first embodiment hereof, the present disclosure provides a delivery system for delivery of a device to a body lumen. The device includes an inflow end and an outflow end, a central lumen therethrough, a plurality of first attachment members located at or near the inflow end, and a plurality of second attachment members located at or near the outflow end. The delivery system includes an inner shaft having a distal tip, an outer shaft slidingly disposed over the inner shaft, and a retractable sheath slidingly disposed over the outer shaft to hold the device in a radially compressed configuration for delivery to a body lumen. The inner shaft includes a coil proximal to the distal tip. The coil is configured for engagement through openings in the plurality of second attachment members on the device, and includes at least a first complete winding configured about a longitudinal axis of the intermediate shaft. The outer shaft includes a coil on a distal end thereof. The coil is configured for engagement through openings in the plurality of first attachment members on the device, and includes at least a first complete winding configured about a longitudinal axis of the outer shaft.

In an aspect of the first embodiment, and in combination with any other aspects herein, the disclosure provides that the inner shaft is rotatable relative to the outer shaft in order to release the plurality of second attachment members.

In an aspect of the first embodiment, and in combination with any other aspects herein, the disclosure provides that the outer shaft is rotatable relative to the retractable sheath and the inner shaft in order to release the plurality of first attachment members.

In an aspect of the first embodiment, and in combination with any other aspects herein, the disclosure provides that the delivery system further includes the device. In an embodiment, the device is self-expandable. In an embodiment, the device includes a prosthetic valve component that is attached within the central lumen of the device.

In an aspect of the first embodiment, and in combination with any other aspects herein, the disclosure provides that the coil of the inflow capture device includes at least the first complete winding configured about a longitudinal axis of the outer shaft and a second complete winding configured about the longitudinal axis of the outer shaft. When the device is in the radially compressed configuration, the first attachment members are attached to the first and second complete windings of the coil in a non-consecutive manner.

In an aspect of the first embodiment, and in combination with any other aspects herein, the disclosure provides that the plurality of first attachment members include at least a first set of first attachment members and a second set of first attachment members. Each attachment member of the first set of first attachment members is disposed adjacent to at least one attachment member of the second set of first attachment members. When the device is in the radially compressed configuration, the first complete winding of the coil engages through openings in the first set of the first attachment members and the second complete winding of the coil engages through openings in the second set of first attachment members.

In an aspect of the first embodiment, and in combination with any other aspects herein, the disclosure provides that the plurality of first attachment members include at least a first set of first attachment members and a second set of first attachment members. Each attachment member of the first set of first attachment members is disposed between two attachment members of the second set of first attachment members. When the device is in the radially compressed configuration, the first complete winding of the coil engages through openings in the first set of the first attachment members and the second complete winding of the coil engages through openings in the second set of first attachment members.

In an aspect of the first embodiment, and in combination with any other aspects herein, the disclosure provides that the coil of the outflow capture device includes at least the first complete winding configured about a longitudinal axis of the inner shaft and a second complete winding configured about the longitudinal axis of the inner shaft. When the device is in the radially compressed configuration, the second attachment members are attached to the first and second complete windings of the coil in a non-consecutive manner.

In an aspect of the first embodiment, and in combination with any other aspects herein, the disclosure provides that the plurality of second attachment members include at least a first set of second attachment members and a second set of second attachment members. Each attachment member of the first set of second attachment members is disposed adjacent to at least one attachment member of the second set of second attachment members. When the device is in the radially compressed configuration, the first complete winding of the coil engages through openings in the first set of the second attachment members and the second complete winding of the coil engages through openings in the second set of second attachment members.

In an aspect of the first embodiment, and in combination with any other aspects herein, the disclosure provides that the plurality of second attachment members include at least a first set of second attachment members and a second set of second attachment members. Each attachment member of the first set of first attachment members is disposed between two attachment members of the second set of first attachment members. When the device is in the radially compressed configuration, the first complete winding of the coil engages through openings in the first set of the second attachment members and the second complete winding of the coil engages through openings in the second set of second attachment members.

In an aspect of the first embodiment, and in combination with any other aspects herein, the disclosure provides that the coil of the outflow capture device includes a polymeric sleeve disposed over an outer surface thereof.

In an aspect of the first embodiment, and in combination with any other aspects herein, the disclosure provides that the plurality of first attachment members include loops and the plurality of second attachment members include loops.

According to a second embodiment hereof, the present disclosure provides that a delivery system includes an inner shaft having a distal tip, an intermediate shaft slidingly disposed over the inner shaft, an outer shaft slidingly disposed over the intermediate shaft, and a retractable sheath slidingly disposed over the outer shaft to hold the device in a radially compressed configuration for delivery to a body lumen. The intermediate shaft includes an outflow capture device mounted on a distal end thereof. The outflow capture device is configured for engagement through openings in the plurality of second attachment members on the device. The outer shaft includes a coil on a distal end thereof. The coil is configured for engagement through openings in the plurality of first attachment members on the device, and includes at least a first complete winding configured about a longitudinal axis of the outer shaft.

In an aspect of the second embodiment, and in combination with any other aspects herein, the disclosure provides that the intermediate shaft is retractable relative to the inner shaft and to the outer shaft in order to release the plurality of second attachment members.

In an aspect of the second embodiment, and in combination with any other aspects herein, the disclosure provides that the outflow capture device includes a plurality of distally extending fingers, the plurality of distally extending fingers configured for engagement through openings in the plurality of second attachment members on the device and the plurality of distally extending fingers being mounted on the intermediate shaft to be retractable therewith.

In an aspect of the second embodiment, and in combination with any other aspects herein, the disclosure provides that the intermediate shaft is rotatable relative to the inner shaft and to the outer shaft in order to release the plurality of second attachment members.

In an aspect of the second embodiment, and in combination with any other aspects herein, the disclosure provides that the outflow capture device includes a coil, and the coil includes at least a first complete winding configured about a longitudinal axis of the intermediate shaft and the coil being mounted on the intermediate shaft to be rotatable therewith.

In an aspect of the second embodiment, and in combination with any other aspects herein, the disclosure provides that the coil of the outflow capture device includes a polymeric sleeve disposed over an outer surface thereof.

In an aspect of the second embodiment, and in combination with any other aspects herein, the disclosure provides that a deflector having a tapered outer surface is mounted on the intermediate shaft adjacent to a proximal end of the coil.

In an aspect of the second embodiment, and in combination with any other aspects herein, the disclosure provides that the delivery system further includes the device, and the coil of the outflow capture device includes at least the first complete winding configured about a longitudinal axis of the inner shaft and a second complete winding configured about the longitudinal axis of the inner shaft. When the device is in the radially compressed configuration, the second attachment members are attached to the first and second complete windings of the coil in a non-consecutive manner. complete winding of the coil engages through openings in the second set of second attachment members.

In an aspect of the second embodiment, and in combination with any other aspects herein, the disclosure provides that the plurality of second attachment members include at least a first set of second attachment members and a second set of second attachment members. Each attachment member of the first set of second attachment members is disposed adjacent to at least one attachment member of the second set of second attachment members. When the device is in the radially compressed configuration, the first complete winding of the coil engages through openings in the first set of the second attachment members and the second complete winding of the coil engages through openings in the second set of second attachment members.

In an aspect of the second embodiment, and in combination with any other aspects herein, the disclosure provides that the plurality of second attachment members include at least a first set of second attachment members and a second set of second attachment members. Each attachment member of the first set of first attachment members is disposed between two attachment members of the second set of first attachment members. When the device is in the radially compressed configuration, the first complete winding of the coil engages through openings in the first set of the second attachment members and the second complete winding of the coil engages through openings in the second set of second attachment members.

In an aspect of the second embodiment, and in combination with any other aspects herein, the disclosure provides that the outer shaft is rotatable relative to the retractable sheath and the intermediate shaft in order to release the plurality of first attachment members.

In an aspect of the second embodiment, and in combination with any other aspects herein, the disclosure provides that the delivery system further includes the device. In an embodiment, the device is self-expandable. In an embodiment, the device includes a prosthetic valve component that is attached within the central lumen of the device.

In an aspect of the second embodiment, and in combination with any other aspects herein, the disclosure provides that the coil of the inflow capture device includes at least the first complete winding configured about a longitudinal axis of the outer shaft and a second complete winding configured about the longitudinal axis of the outer shaft. When the device is in the radially compressed configuration, the first attachment members are attached to the first and second complete windings of the coil in a non-consecutive manner.

In an aspect of the second embodiment, and in combination with any other aspects herein, the disclosure provides that the plurality of first attachment members include at least a first set of first attachment members and a second set of first attachment members. Each attachment member of the first set of first attachment members is disposed adjacent to at least one attachment member of the second set of first attachment members. When the device is in the radially compressed configuration, the first complete winding of the coil engages through openings in the first set of the first attachment members and the second complete winding of the coil engages through openings in the second set of first attachment members.

In an aspect of the second embodiment, and in combination with any other aspects herein, the disclosure provides that the plurality of first attachment members include at least a first set of first attachment members and a second set of first attachment members. Each attachment member of the first set of first attachment members is disposed between two attachment members of the second set of first attachment members. When the device is in the radially compressed configuration, the first complete winding of the coil engages through openings in the first set of the first attachment members and the second complete winding of the coil engages through openings in the second set of first attachment members.

In an aspect of the second embodiment, and in combination with any other aspects herein, the disclosure provides that the plurality of first attachment members include loops and the plurality of second attachment members include loops.

According to a third embodiment hereof, the present disclosure provides that a delivery system includes a first shaft including an outflow capture device mounted on a distal end thereof, a second shaft slidingly disposed over the first shaft and including an inflow capture device mounted on a distal end thereof, and a retractable sheath slidingly disposed over the second shaft to hold the device in a radially compressed configuration for delivery to a body lumen. The outflow capture device is configured for engagement through openings in the plurality of second attachment members on the device. The inflow capture device is configured for engagement through openings in the plurality of first attachment members on the device.

In an aspect of the third embodiment, and in combination with any other aspects herein, the disclosure provides that the first shaft includes a distal tip attached thereto and the first shaft is rotatable relative to the second shaft in order to release the plurality of second attachment members.

In an aspect of the third embodiment, and in combination with any other aspects herein, the disclosure provides that the outflow capture device is a coil that includes at least a first complete winding configured about a longitudinal axis of the first shaft and the coil being mounted on the first shaft to be rotatable therewith, and the inflow capture device is a coil that includes at least a first complete winding configured about a longitudinal axis of the second shaft and the coil being mounted on the second shaft to be rotatable therewith.

In an aspect of the third embodiment, and in combination with any other aspects herein, the disclosure provides that the delivery system further includes a third shaft including a distal tip attached thereto. The first shaft is slidingly disposed over the third shaft. In an embodiment, the first shaft is retractable relative to the third shaft and to the second shaft in order to release the plurality of second attachment members.

In an aspect of the third embodiment, and in combination with any other aspects herein, the disclosure provides that the outflow capture device includes a plurality of distally extending fingers, the plurality of distally extending fingers configured for engagement through openings in the plurality of second attachment members on the device and the plurality of distally extending fingers being mounted on the first shaft to be retractable therewith.

In an aspect of the third embodiment, and in combination with any other aspects herein, the disclosure provides that the first shaft is rotatable relative to the third shaft and to the second shaft in order to release the plurality of second attachment members.

In an aspect of the third embodiment, and in combination with any other aspects herein, the disclosure provides that the outflow capture device is a coil that includes at least a first complete winding configured about a longitudinal axis of the first shaft and the coil being mounted on the first shaft to be rotatable therewith. The inflow capture device is a coil that includes at least a first complete winding configured about a longitudinal axis of the second shaft and the coil being mounted on the second shaft to be rotatable therewith.

According to a fourth embodiment hereof, the present disclosure provides methods of delivering a prosthetic valve device to a treatment site within a body lumen. A delivery system having the prosthetic valve device loaded thereon is advanced through a vasculature. A plurality of first attachment members of the prosthetic valve device located at or near an inflow end of the prosthetic valve device is attached to an inflow capture device of the delivery system and a plurality of second attachment members of the prosthetic valve device located at or near an outflow end of the prosthetic valve device is attached to an outflow capture device of the delivery system. The prosthetic valve device is held in a radially compressed configuration within a retractable sheath of the delivery system. The prosthetic valve device is positioned at the treatment site. The retractable sheath of the delivery system is retracted to expose the outflow end of the prosthetic valve device, with the plurality of second attachment members of the prosthetic valve device remaining attached to the outflow capture device of the delivery system. The outflow capture device is moved to release the plurality of second attachment members of the prosthetic valve device, thereby allowing the outflow end of the prosthetic valve device to radially expand. The retractable sheath of the delivery system is further retracted to expose the inflow end of the prosthetic valve device, with the plurality of first attachment members of the prosthetic valve device remaining attached to the inflow capture device of the delivery system. The inflow capture device is moved to release the plurality of first attachment members of the prosthetic valve device, thereby allowing the inflow end of the prosthetic valve device to radially expand.

In an aspect of the fourth embodiment, and in combination with any other aspects herein, the disclosure provides that the method further includes adjusting a position of the prosthetic valve device after the step of retracting the retractable sheath of the delivery system to expose the outflow end of the prosthetic valve device.

In an aspect of the fourth embodiment, and in combination with any other aspects herein, the disclosure provides that the step of adjusting a position of the prosthetic valve device includes distally advancing the retractable sheath over the outflow end of the prosthetic valve device.

In an aspect of the fourth embodiment, and in combination with any other aspects herein, the disclosure provides that the inflow capture device includes a coil and the step of moving the inflow capture device includes rotating the coil.

In an aspect of the fourth embodiment, and in combination with any other aspects herein, the disclosure provides that the outflow capture device includes a coil and the step of moving the outflow capture device includes rotating the coil.

In an aspect of the fourth embodiment, and in combination with any other aspects herein, the disclosure provides that the outflow capture device includes a plurality of distally extending fingers and the step of moving the outflow capture device includes retracting the distally extending fingers.

In an aspect of the fourth embodiment, and in combination with any other aspects herein, the disclosure provides that the treatment site is a pulmonary valve.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant arts to make, use, and implant the prosthesis described herein. In the drawings, like reference numbers indicate identical or functionally similar elements.

DETAILED DESCRIPTION OF THE INVENTION

Figure 1:
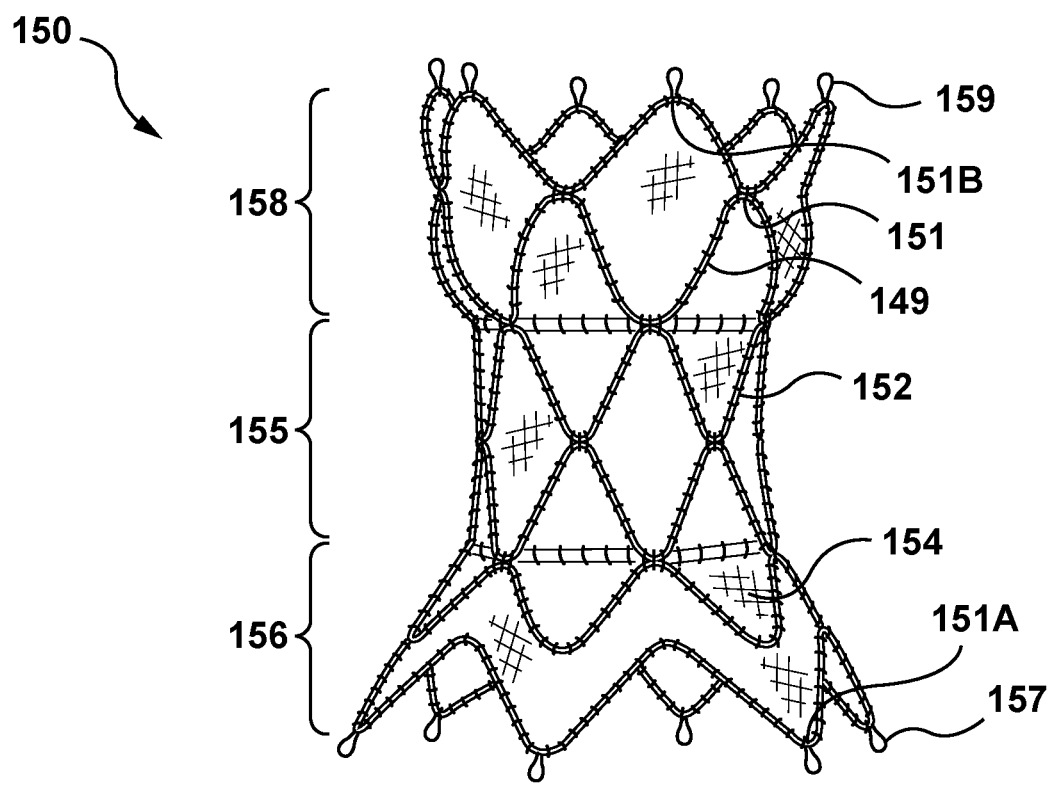
FIG. 1 is a side view of an exemplary prosthetic valve device that may be utilized in embodiments hereof.

Specific embodiments of the present invention are now described with reference to the figures, wherein like reference numbers indicate identical or functionally similar elements. Unless otherwise indicated, the terms "distal" and "proximal", when used in the following description to refer to a shaft, a sheath, or a delivery device, are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician. The terms "distal" and "proximal", when used in the following description to refer to a device to be implanted into a vessel, such as a heart prosthetic valve device, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

In addition, the term "self-expanding" is used in the following description with reference to one or more stent structures of the prostheses hereof and is intended to convey that the structures are shaped or formed from a material that can be provided with a mechanical memory to return the structure from a radially compressed or constricted radially compressed configuration to a radially expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Embodiments hereof relate to a delivery system for delivery of a prosthetic valve device to a body lumen. The prosthetic valve device includes a plurality of first attachment members located at or near its inflow end, and a plurality of second attachment members located at or near its outflow end. The delivery system includes at least a first shaft including an outflow capture device mounted on a distal end thereof, a second shaft slidingly disposed over the first shaft and including an inflow capture device mounted on a distal end thereof, and a retractable sheath slidingly disposed over the second shaft to hold the prosthetic valve device in a radially compressed configuration for delivery to a body lumen. The outflow capture device is configured for engagement through openings in the plurality of second attachment members on the prosthetic valve device, and the inflow capture device is configured for engagement through openings in the plurality of first attachment members on the prosthetic valve device. The outflow capture device is configured to restrain the outflow end of the prosthetic valve device after the retractable sheath has been retracted to expose the outflow end of the prosthetic valve device in situ, and similarly the inflow capture device is configured to restrain the inflow end of the prosthetic valve device after the retractable sheath has been retracted to expose the inflow end of the prosthetic valve device in situ. The inflow and outflow capture devices provide for controlled release of the inflow and outflow ends, respectively, of the prosthetic valve device. More particularly, each of the inflow and outflow capture devices improve control and alignment during deployment and positioning of the prosthetic valve device, and each of the inflow and outflow capture devices can release the captured end of the prosthetic valve device at any time during deployment to suit any number of system characteristics driven by the therapy type, device type, or specific anatomical conditions that may prescribe the release timing. Typically, each of the inflow and outflow capture devices capture release is activated after at least partial retraction of the retractable sheath, and thus provides a means of restraining the prosthetic valve device during positioning. Additional restraint of the prosthetic valve device is a key characteristic when the operator is attempting to accurately position the prosthetic valve device relative to an anatomical target. The outflow capture device in particular mitigates backfolding and/or infolding of the prosthetic valve device that may otherwise occur during deployment.

The principles of the invention may be practiced in any instance in which it is desired to deliver a medical device intraluminally to a desired anatomic site. For the purpose of discussion, the invention will generally be described in the context in which the medical device being loaded onto a delivery system and delivered intraluminally is a prosthetic valve. In an embodiment, the prosthetic valve is an infundibular reducer device configured to be implanted in the right ventricular outflow tract or the infundibulum, and corresponding embodiments of the invention are particularly useful for delivering the infundibular reducer device to the right ventricular outflow tract. The prosthetic valve device may be used in anatomic locations other than the infundibulum, such as the right ventricular outflow tract and other locations in or near the heart. The purpose of such devices is to allow replacement or prosthetic valves, such as pericardial heart valves, for example, having a smaller diameter than the diameter of the implanted site (e.g., the right ventricular outflow tract) to be implanted. However, other uses of the invention, such as to deliver different medical devices to different locations in the body, are contemplated and are not limited to those discussed in the application.

Figure 1A:
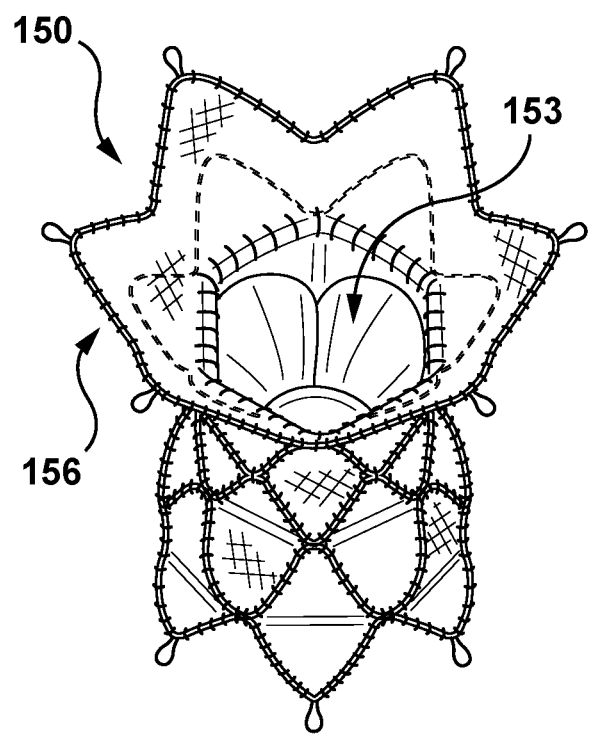
FIG. 1A is a perspective view of the prosthetic valve device of FIG. 1.
Figure 1B:
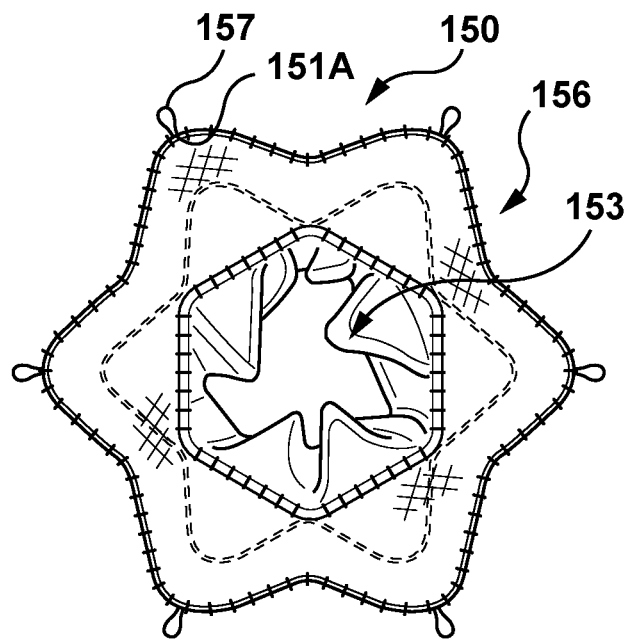
FIG. 1B is an end view of the prosthetic valve device of FIG. 1.

FIG. 1 is a side view of an exemplary prosthetic valve device 150 that may be deployed using embodiments of delivery systems described herein, while FIGS. 1A and 1B are perspective and end views, respectively, of the prosthetic valve device 150. The prosthetic valve device 150 is merely exemplary. It is understood that any number of alternate devices can be used with the delivery devices and methods described herein. For example, U.S. Pat. No. 8,801,776 to House et al., herein incorporated by reference in its entirety, describes a device that may be delivered by delivery systems described herein. In an embodiment, the prosthetic valve device 150 is the Medtronic HARMONY™ transcatheter pulmonary valve. In addition, the delivery systems described herein may also be used with other self-expanding prostheses such as other prosthetic heart valves, stent-graft prostheses, uncovered stents, bare metal stents, drug eluting stents, and any self-expanding structure.

The prosthetic valve device 150 includes an expandable stent or frame 152 that supports a prosthetic valve component 153 within the interior of the stent 152. In embodiments hereof, the stent 152 is self-expanding or self-expandable to return to a radially expanded configuration from a radially compressed or constricted radially compressed configuration. The prosthetic valve device 150 is compressible to be mounted into a delivery system and expandable to fit a desired body lumen, such as the right ventricular outflow tract, for example. In the embodiment depicted in FIG. 1, the stent 152 has an expanded, longitudinally asymmetric hourglass configuration including three longitudinal sections or portions of a relatively enlarged inflow end 156, a relatively enlarged outflow end 158, and a midportion 155 extending between the first and second ends 156, 158. The inflow end 156 may also be referred to herein as the proximal or first end, and the outflow end 158 may also be referred to herein as the distal or second end. The midportion 155 is generally cylindrical in shape with a smaller diameter than the inflow and outflow ends 156, 158. Each longitudinal section or portion of stent 152 may be designed with a number of different configurations and sizes to meet the different requirements of the location in which it may be implanted. Each longitudinal section or portion of the stent 152 may have the same or different cross-portion which may be for example circular, ellipsoidal, rectangular, hexagonal, rectangular, square, or other polygonal shape, although at present it is believed that circular or ellipsoidal may be preferable when the prosthetic valve device is being provided for replacement of the aortic or mitral valve. As alternatives to the deployed asymmetric hourglass configuration of FIG. 1, the stent 152 may have a symmetric hourglass configuration, a generally tubular configuration, or other stent configuration or shape known in the art for valve replacement.

One advantage of the midportion 155 having a smaller diameter than the inflow and outflow ends 156, 158 is to allow at least a portion of the midportion 155 of the stent 152 to hold or retain the prosthetic valve component 153 in its central lumen, when the prosthetic valve component 153 has a smaller diameter than the lumen in which the prosthetic valve device 150 is to be placed. The larger diameters of the inflow and outflow ends 156, 158 allow the prosthetic valve device 150 to be secured in place in a tubular organ, or a valved anatomic site, having a diameter larger than that of the prosthetic valve component 153 but smaller than the expanded diameter of the inflow and outflow ends 156, 158. The inflow and outflow ends 156, 158 are also shown to be flared, such that they gradually increase in diameter from where the inflow and outflow 156, 158 extend from the midportion 155. The angle at which the inflow and outflow ends 156, 158 are flared from the midportion 155 can vary depending on the desired maximum diameter and desired length of the stent 152.

The stent 152 includes a plurality of crowns 151 and a plurality of struts 149 with each crown 151 being formed between a pair of opposing struts 149. Each crown 151 is a curved segment or bend extending between opposing struts 149. A plurality of side openings are defined by the plurality of crowns 151 and the plurality of struts 149. A series of endmost inflow crowns 151A are formed at the inflow end 156 of the stent 152. The number of endmost inflow crowns 151A may vary according to size and application and may range, for example, between 6-15 crowns. In an embodiment, the inflow end 156 of the stent 152 has a total of six endmost inflow crowns 151A, as best shown in the end view of FIG. 1B. However, the configuration of the stent 152 is exemplary and other stent configurations are contemplated. For example, in another embodiment hereof as shown in FIG. 9C, a stent 152C has a total of nine endmost inflow crowns 151C. Similarly, a series of endmost outflow crowns 151B are formed at the outflow end 158 of the stent 152. The number of endmost outflow crowns 151B may vary according to size and application and may range, for example, between 6-15 crowns. In an embodiment, the outflow end 158 of the stent 152 has a total of six endmost outflow crowns 151B. However, the configuration of the stent 152 is exemplary and other stent configurations are contemplated. For example, in another embodiment hereof as shown in FIG. 9C, the stent 152C has a total of nine endmost outflow crowns 151D.

As previously mentioned, the prosthetic valve device 150 includes the prosthetic valve component 153 positioned within the center lumen of the stent 152. The prosthetic valve component 153 is attached to (i.e., affixed to, held by, retained by, etc.) the stent 152 along its edges and is sutured or otherwise attached within the stent 152. The prosthetic valve component 153 is capable of blocking flow in one direction to regulate flow there through via valve leaflets that may form a bicuspid or tricuspid replacement valve. In the embodiment of FIGS. 1, 1A, and 1B, the prosthetic valve component 153 includes three leaflets or a tricuspid leaflet configuration, although a bicuspid leaflet configuration may alternatively be used in embodiments hereof. The prosthetic valve component 153 included in the prosthetic valve device 150 may be a preserved bovine jugular vein of the type described in the above-cited Tower et al. references. Other vessels or donor species may, however, alternatively be employed. Alternatively, other substantially tubular valve bodies may be the prosthetic valve component 153 of the invention. For example, the prosthetic valve component 153 may be formed from a variety of materials including biological materials and polymers. Biological material includes homograft, allograft, or xenograft, with xenograft being common and well accepted and usually from bovine, ovine, swine or porcine pericardium, or a combination thereof. Polymers include expanded TEFLON™ polymers, high density polyethylene, polyurethane, and combinations thereof. Some examples of prosthetic valve components that may be used in the invention are described in U.S. Pat. Nos. 6,719,789 and 5,480,424, issued to Cox, which are incorporated herein by reference.

Graft material 154 encloses or lines the stent 152 as would be known to one of ordinary skill in the art of prosthetic tissue valve construction. The graft material 154 may be a natural or biological material such as pericardium or another membranous tissue such as intestinal submucosa. Alternatively, the graft material 154 may be a low-porosity woven fabric, such as polyester, Dacron fabric, or PTFE, which creates a one-way fluid passage when attached to the stent. In one embodiment, the graft material 154 may be a knit or woven polyester, such as a polyester or PTFE knit, which can be utilized when it is desired to provide a medium for tissue ingrowth and the ability for the fabric to stretch to conform to a curved surface, or may instead be ultra-high molecular weight polyethylene (UHMWPE), cotton, or the like. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

The prosthetic valve device 150 includes a plurality of first attachment members 157 on or near the inflow end 156 and a plurality of second attachment members 159 on or near the outflow end 158. More particularly, a first attachment member 157 is attached to each endmost inflow crown 151A on or near the inflow end 156 and a second attachment member 159 is attached to each endmost outflow crown 151B. Thus, the number of total attachment members are dependent upon the design and configuration of the prosthetic valve device 150, and thus may be higher or lower than shown in the embodiment of FIG. 1. Each attachment member of the first and second attachment members 157, 159 define an opening. Such attachment members may be loops formed from sutures, may be formed from the material used to form part of the stent 152, or other materials. The attachment members may be made of loops formed from UHMWPE thread, for one example, since this material advantageously has the properties of being durable and lubricous, as well as hydrophobic, which can help to minimize swelling or clotting due to contact with blood. However, other materials may be used that comprise some or all of these attachment properties. Other attachment members besides loops are also contemplated by the invention. Such attachment members are configured to connect, fasten or attach the prosthetic valve device 150 to a delivery system, allow for collapse of the prosthetic valve device 150 for insertion into the body, and also are configured to be selectively disengaged or disconnected from the delivery system in order to release the prosthetic valve device 150 at a desired anatomic site as will be described in more detail herein.

Although described above that an attachment member is attached to each endmost crown of the inflow and outflow ends of the prosthetic valve device 150, it will be understood by one of ordinary skill in the art that not all endmost crowns are required to be attached to a delivery system during delivery and thus not all endmost crowns are required to include an attachment member attached thereto. Further, in an embodiment, all endmost crowns may include an attachment member attached thereto but not all attachment members are required to be loaded onto the delivery system.

Figure 2:
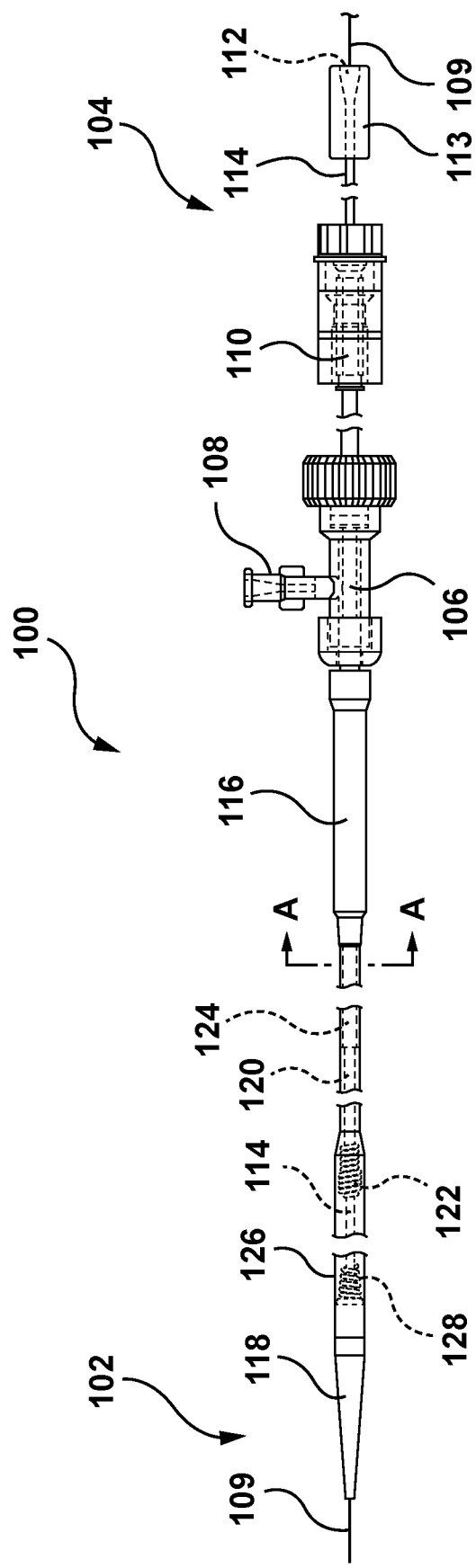
FIG. 2 is a side view of a delivery system according to an embodiment hereof, wherein the delivery system includes an inflow capture device configured to engage an inflow end of a prosthetic valve device and an outflow capture device configured to engage an outflow end of the prosthetic valve device when the prosthetic valve device is loaded within the delivery system.

FIG. 2 is a side view of a delivery system 100 according to an embodiment hereof. The delivery system 100 is configured to receive the prosthetic valve device 150 and percutaneously deliver the prosthetic valve device 150 in a compressed or radially compressed configuration to a treatment site in situ. More particularly, the delivery system 100 includes an inflow capture device 122 configured to engage or attach to the plurality of first attachment members 157 on or near the inflow end 156 of the prosthetic valve device 150 and an outflow capture device 128 configured to engage or attach to the plurality of second attachment members 159 on or near the outflow end 158 of the prosthetic valve device 150. In the embodiment of FIGS. 2-13, the outflow capture device 128 is a coil configured for engagement through openings in the plurality of second attachment members 159 that is rotatable to release the plurality of second attachment members 159 and the inflow capture device 122 is also a coil configured for engagement through openings in the plurality of first attachment members 157 that is rotatable to release the plurality of first attachment members 157. Components of the delivery system 100 are first described with respect to FIGS. 2-4, and steps involving loading the prosthetic valve device 150 on the delivery system 100 and delivering the prosthetic valve device 150 are shown and described with respect to FIGS. 5-13.

FIG. 2 illustrates the delivery system 100 disposed over a guidewire 109 for illustrative purposes only. With any of the systems and methods described herein, the guidewire 109 may be initially introduced into the target treatment site through a suitable body lumen to properly locate the desired position for the prosthetic valve device 150. The remainder of the delivery system 100 may then be guided along the guidewire 109 and into the site. The guidewire 109 may be, for example a 0.089 cm extra stiff guidewire as manufactured by Amplatzer, Golden Valley, Minn., U.S.A.

The delivery system 100 includes a distal end generally designated by the reference numeral 102 and a proximal end generally designated by the reference number 104. The proximal end 104 of the delivery system 100 remains outside of the patient, and the distal end 102 is inserted into the patient and is delivered intravascularly to an area at or near a pulmonary valve inside the body. Other uses for the delivery system 100 in other areas of the body, however, are also contemplated. The proximal end 104 includes means for remotely controlling the distal end 102 of the delivery system 100, in particular relating to deploying or releasing the prosthetic valve device 150 from the delivery system 100 in situ.

The components of the proximal end 104 of the delivery system 100 may include those shown in FIG. 2, although additional and/or alternative components are also contemplated. The proximal end 104 includes a first rotating homeostasis valve 106, a side access port 108, a second rotating homeostasis valve 110, and a handle 113 including a guidewire lumen inlet 112. The first rotating homeostasis valve 106 grips or forms a fluid seal around an outer surface of the delivery system 100 to prevent blood or other fluid from leaking out of the delivery device at the proximal end or entry site into a patient and is configured to allow wires, devices and fluid to pass through. Furthermore, the first rotating homeostasis valve 106 also controls the components of the distal end as described in more detail below by rotation of a portion of the first rotating homeostasis valve 106. The side access port 108 is provided as a means for injecting contrast media or saline, for example, into the delivery system 100. The second rotating homeostasis valve 110 also prevents blood or other fluid from leaking back through the delivery system 100 and is configured to allow wires, devices, and fluid to pass through. Furthermore, the second rotating homeostasis valve 110 also controls the components of the distal end as described in more detail below by rotation of a portion of the second rotating homeostasis valve 110. The first and second valves rotating homeostasis valve 106, 110 are exemplary. Other alternative or additional components of the proximal end 104 of the delivery system 100 are also contemplated by the invention.

Figure 2A:
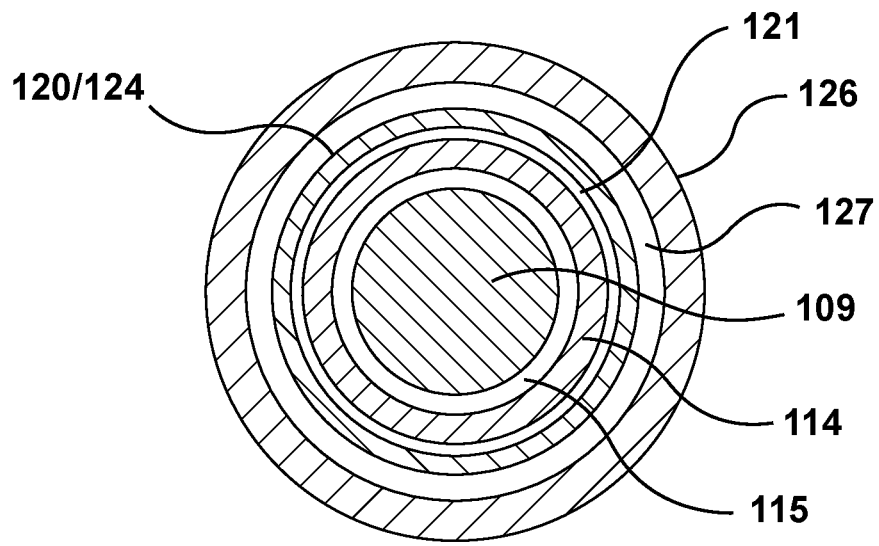
FIG. 2A is a cross-sectional view of the delivery system of FIG. 2 taken along line A-A of FIG. 2.

FIG. 2 shows the distal end 102 of the delivery system 100 in an assembled configuration, without a prosthetic valve device attached or loaded. FIG. 2A is a cross-sectional view of the delivery system of FIG. 2 taken along line A-A of FIG. 2. As best shown on FIG. 2A, the delivery system 100 includes at least three concentric tubular components. More particularly, the delivery system 100 includes an inner shaft 114 which defines a guidewire lumen 115, an outer shaft 120 which defines a lumen 121 and is slidingly disposed over the inner shaft 114, and a retractable sheath 126 which defines a lumen 127 and is slidingly disposed over the outer shaft 120 to hold the prosthetic valve device 150 in a radially collapsed or compressed configuration during delivery. The retractable sheath 126 is made of a low friction and flexible material, such as polytetrafluoroethylene (PTFE), polyurethane, silicone, or polyethylene is retractable via a retraction mechanism such as a knob of the first rotating homeostasis valve 106. Various other retraction mechanisms may be used, such as an axially-slidable lever, a rotatable rack and pinion gear, or other known mechanisms. In this way, the retractable sheath 126 is retractable relative to the inner and outer shafts 114, 120 during deployment of the prosthetic valve device 150. The delivery system 100 may further include an outer sleeve 116 that is disposed over a proximal portion of the retractable sheath 126. The purpose of the sleeve 116 is to keep blood from leaking back around the delivery system 100.

A tapered distal tip 118 is attached to the inner shaft 114 and serves to ease the passage of the delivery system 100 through the vasculature. The inner shaft 114 extends along the entire length of the delivery system 100 and is configured to be tracked over the guidewire 109. The inner shaft 114 may be formed of one or more polymeric materials, non-exhaustive examples of which include polyethylene, polyethylene block amide copolymer (PEBA), polyamide and/or combinations thereof, either laminated, blended or co-extruded. Optionally, the inner shaft 114 may be formed as a composite having a reinforcement layer incorporated within a polymeric body in order to enhance strength and/or torque-ability. Suitable reinforcement layers include braiding, wire mesh layers, embedded axial wires, embedded helical or circumferential wires, hypotubes, and the like. The inner shaft 114 is attached to the handle 113 at its proximal end. The handle 113 includes the guidewire lumen inlet 112 such that the handle 113 and the inner shaft 114 may be tracked over the guidewire 109. Inner shaft 114 may be independently advanced or retracted through other components of the delivery system 100 by moving the handle 113 to which it is attached. In addition, the inner shaft 114 may be independently rotated relative to the other components of the delivery system 100 by rotating or turning the handle 113 to which it is attached. In an embodiment, the handle 113 may include an actuator (not shown) such as a knob that is operatively coupled to the inner shaft 114 such that rotation of the actuator results in rotation of the inner shaft 114.

Figure 3:
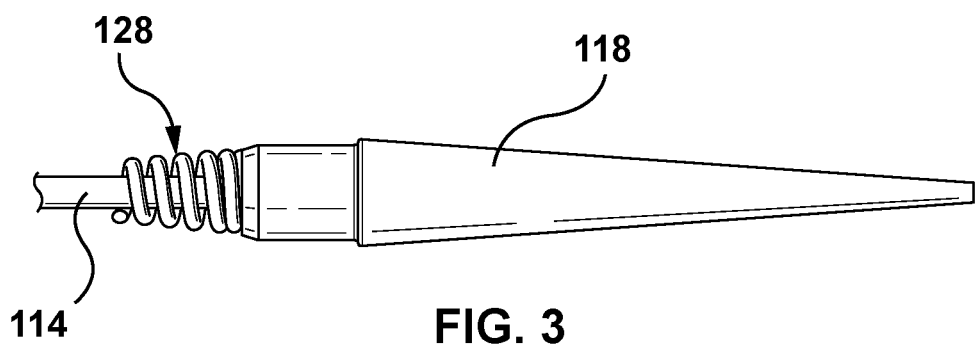
FIG. 3 is an enlarged side perspective view of a distal tip of the delivery system of FIG. 2.

In this embodiment, as best shown in FIG. 3 which is an enlarged side perspective view of the distal tip 118, the outflow capture device 128 is coupled to a distal end of the inner shaft 114. More particularly, the outflow capture device 128 is attached to a proximal end of the distal tip 118, and the distal tip 118 is attached or secured to the distal end of the inner shaft 114. When the inner shaft 114 is rotated by rotating or turning the handle 113 to which it is attached, the inner shaft 114, the distal tip 118 and the outflow capture device 128 collectively rotate as an assembly. Thus, movement of the inner shaft 114, as controlled by the handle 113, controls movement or rotation of the outflow capture device 128. In this embodiment, the outflow capture device 128 is a coil including at least one complete winding about a longitudinal axis of the inner shaft 114 and is configured for engagement through openings in the plurality of second attachment members 159 as will be described in more detail with respect to FIG. 7. In an embodiment, the coil of the outflow capture device 128 has an overall tapered profile with a distal end thereof having a larger diameter than a proximal end thereof.

Figure 4:
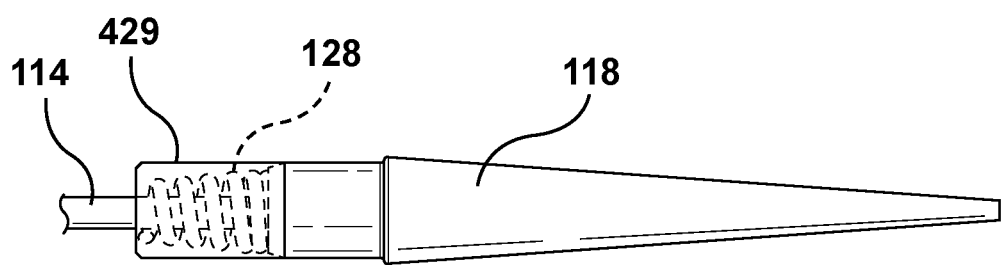
FIG. 4 is an enlarged side perspective view of a distal tip of a delivery system according to another embodiment hereof, wherein the distal tip includes a polymeric sleeve disposed over an outflow capture device of the delivery system.

In an embodiment hereof, as shown in FIG. 4, a relatively short polymeric sleeve 429 may be attached to the proximal end of the distal tip 118. The polymeric sleeve 429 extends in a proximal direction to cover the outflow capture device 128. The polymeric sleeve 429 is disposed over an outer surface of the outflow capture device 128 in order to isolate the outflow capture device 128 from the anatomy in situ after the outflow end 158 of the prosthetic valve device 150 is deployed. The polymeric sleeve 429 is formed from a flexible and soft material that can be rolled, flipped, or other moved distally to expose the outflow capture device 128 when the prosthetic valve device 150 is loaded onto the delivery system as described in more detail with respect to FIG. 7. Only the proximal edge of the coil of the outflow capture device 128 is exposed when loading second attachment members 159 thereon. The polymeric sleeve 429 is configured to not impede the windings of the coil of the outflow capture device 128 during loading and deployment.

The outer shaft 120 is slidingly disposed over the inner shaft 114. The outer shaft 120 may be formed of one or more polymeric materials, non-exhaustive examples of which include polyethylene, polyethylene block amide copolymer (PEBA), polyamide and/or combinations thereof, either laminated, blended or co-extruded. Surrounding the outer shaft 120 is a reinforcement layer 124, which is attached or otherwise bonded to the outer shaft 120 and serves to reinforce the outer shaft 120. Optionally, the outer shaft 120 may be formed as a composite having a reinforcement layer incorporated within a polymeric body in order to enhance strength and/or torque-ability. Suitable reinforcement layers include braiding, wire mesh layers, embedded axial wires, embedded helical or circumferential wires, hypotubes, and the like. Movement of the outer shaft 120 is controlled by the second rotating homeostasis valve 110 at the proximal end 104 of the delivery system 100. A portion of the second rotating homeostasis valve 110 is rotated or otherwise manipulated in order to rotate the outer shaft 120 or move the outer shaft 120 proximally and distally as desired. The inflow capture device 122 is coupled to a distal end of the outer shaft 120. When the outer shaft 120 is rotated by rotating or turning a portion of the second rotating homeostasis valve 110, the outer shaft 120 and the inflow capture device 122 collectively rotate as an assembly. Thus, movement of the outer shaft 120, as controlled by the second rotating homeostasis valve 110, controls movement or rotation of the inflow capture device 122. In this embodiment, the inflow capture device 122 is a coil including at least one complete winding about a longitudinal axis of the outer shaft 120 and is configured for engagement through openings in the plurality of first attachment members 157 as will be described in more detail with respect to FIG. 6.

The inflow and outflow capture devices 122, 128 provides means for releasably attaching the prosthetic valve device 150 onto the delivery system 100 by holding the inflow and outflow ends 156, 158, respectively, of the prosthetic valve device 150 on the delivery system 100 during delivery. The inflow capture device 122 is configured to hold the inflow end 156 of the prosthetic valve device 150 by engaging through openings in the plurality of first attachment members 157, while the outflow capture device 128 is configured to hold the outflow end 158 of the prosthetic valve device 150 by engaging through openings in the plurality of second attachment members 159. The inflow and outflow capture devices 122, 128 are further configured to release the prosthetic valve device 150 from the delivery system 100 in situ. The inner shaft 114 is rotatable in order to release the plurality of second attachment members 159. Stated another way, when the outflow capture device 128 rotates or turns, the plurality of second attachment members 159 disengage or detach from the outflow capture device 128, thus releasing the outflow end 158 of the prosthetic valve device 150. Similarly, the outer shaft 120 is rotatable in order to release the plurality of first attachment members 157. Stated another way, when the inflow capture device 122 rotates or turns, the plurality of first attachment members 157 disengage or detach from the inflow capture device 122, thus releasing the inflow end 156 of the prosthetic valve device 150. The speed that the inflow and outflow ends 156, 158 of the prosthetic valve device 150 are released from the delivery system 100 are controlled by the rate of rotation of the inflow and outflow capture devices 122, 128, respectively, therefore preventing uncontrolled release of the prosthetic valve device 150. The inflow and outflow ends 156, 158 of the prosthetic valve device 150 are selectively held, restrained, or otherwise controlled by the inflow and outflow capture devices 122, 128, respectively, until the accurate positioning of the prosthetic valve device 150 is established. The coils of the inflow and outflow capture devices 122, 128 have opposite winding directions such that the plurality of first attachment members 157 coupled to the inflow capture device 122 move in a distal direction along the coil winding(s) to release the inflow end 156 of the prosthetic valve device 150 while the plurality of second attachment members 159 coupled to the outflow capture device 128 move in a proximal direction along the coil winding(s) to release the outflow end 158 of the prosthetic valve device 150.

Figure 5:
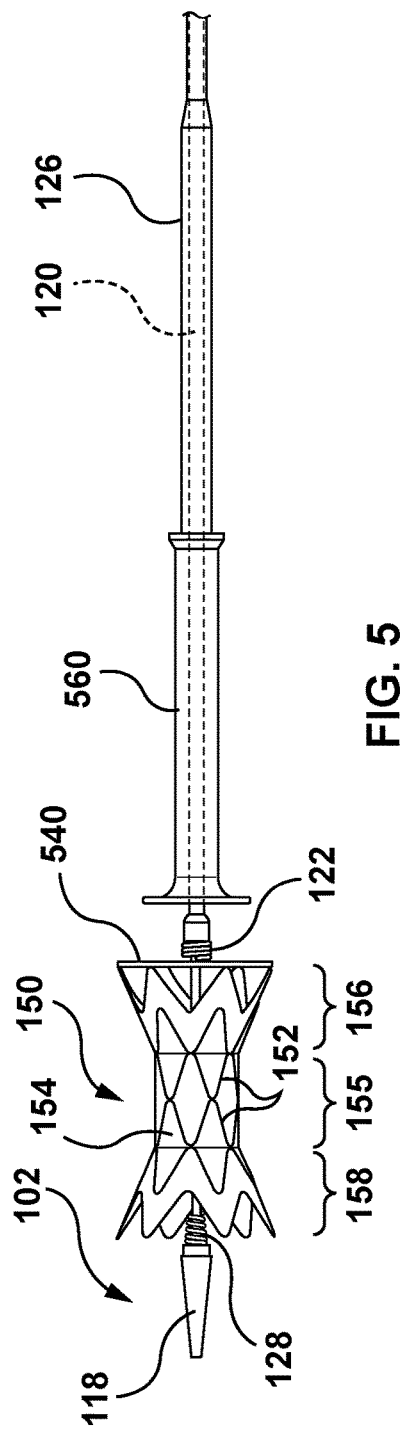
FIG. 5 is a side perspective view of the delivery system of FIG. 2 and the prosthetic valve device of FIG. 1 prior to loading the prosthetic valve device on the delivery system.

FIGS. 5-13 illustrate the steps involved in loading the prosthetic valve device 150 onto the delivery system 100 and delivering the prosthetic valve device 150. FIG. 5 in particular is a side perspective view of the delivery system 100 and illustrates the prosthetic valve device 150 surrounding the distal end 102 of the delivery system 100 prior to loading or attaching the prosthetic valve device 150 onto the delivery system. The prosthetic valve device 150 is shown in its expanded configuration in FIG. 5 and is not yet attached to the delivery system. The loading is done outside the body prior to insertion of the delivery system 100 into a vein or other body lumen. The loading involves extending the distal portion 102 of the delivery system 100, and specifically the inner shaft 114 and the distal tip 118, through a central lumen of the prosthetic valve device 150. As shown in FIG. 5, in order to load or attach the inflow end 156 of the prosthetic valve device 150 to the inflow capture device 122 of the delivery system 100, a loading rail 540 is inserted through the plurality of first attachment members 157 on the inflow end 156 of the prosthetic valve device 150.

Figure 6:
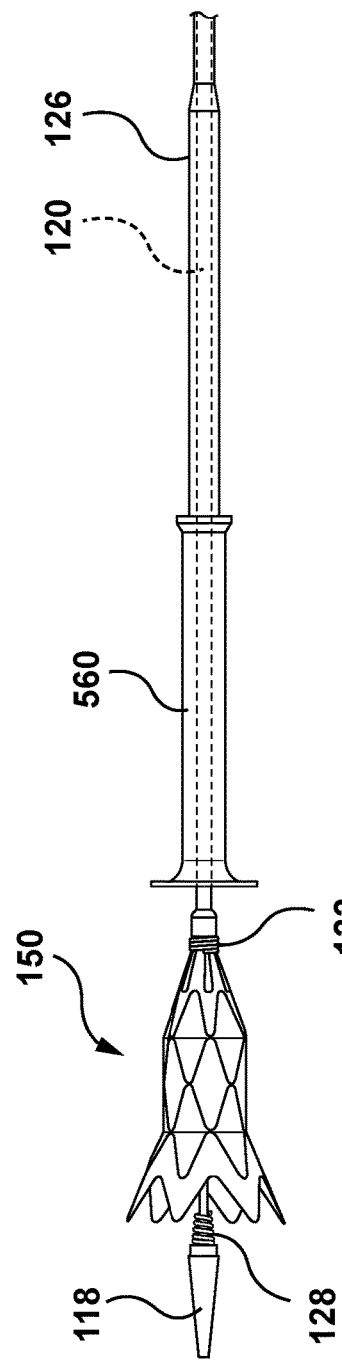
FIG. 6 is a side perspective view of the delivery system of FIG. 2 and the prosthetic valve device of FIG. 1 with the inflow capture device of the delivery system engaged or attached to the inflow end of the prosthetic valve device.

The loading rail 540 is flexible plastic tubing or similar material that is threaded through the plurality of first attachment members 157 at the inflow end 156 of the prosthetic valve device 150. The loading rail 540 has two free ends. Both free ends of the loading rail 540 have a central lumen, hollow area. One of the free ends of the loading rail is cut at an angle to allow ease of insertion into the attachment loops and the other end is square cut to allow that free end to be placed on or otherwise attached to the inflow capture device 122. For example, the loading rail 540 and the inflow capture device 122 can be attached by a frictional fit (e.g., one of the loading rail 540 and inflow capture device 122 can slip over the other to connect the two components). Once the loading rail 540 is connected to the inflow capture device 122, the plurality of first attachment members 157 are each manually pushed one-by-one along the loading rail 540, then onto the inflow capture device 122. As the first attachment members 157 are pushed along and onto the inflow capture device 122, the inflow end 156 of the prosthetic valve device 150 is compressed or collapsed. Once all of the first attachment members 157 are pushed off the loading rail 540 and are loaded onto the inflow capture device 122, the loading rail 540 is removed from the inflow capture device 122. FIG. 6 shows the inflow end 156 of the prosthetic valve device 150 connected to the inflow capture device 122 as described, with the inflow end 156 of the of the prosthetic valve device 150 being compressed to closely match the diameter of the inflow capture device 122.

Figure 6A:
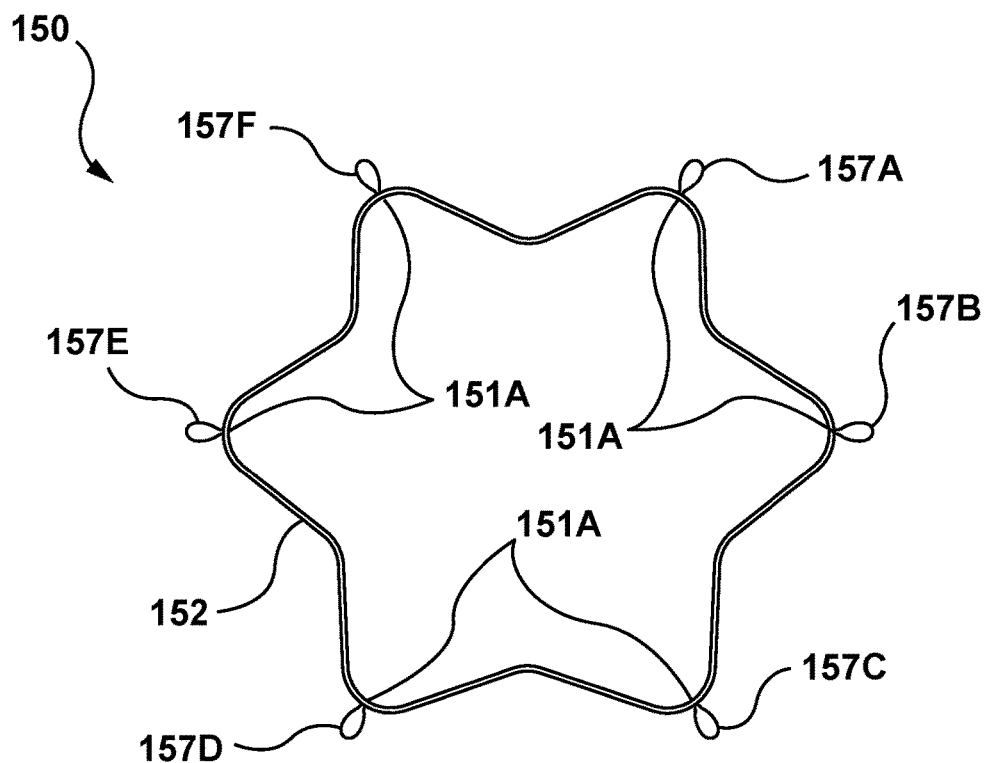
FIG. 6A is an end view illustration of the prosthetic valve device of FIG. 1.

In an embodiment of loading the inflow end 156 of the prosthetic valve device 150, the plurality of first attachment members 157 are manually pushed one-by-one along the loading rail 540, then onto the inflow capture device 122, in consecutive order. More particularly, as shown on FIG. 6A which is an end view illustration of the prosthetic valve device 150 showing the first attachment members 157, the first attachment members 157 may be considered to include a total of six attachment members 157A, 157B, 157C, 157D, 157E, 157F sequentially or consecutively around a perimeter of the inflow end of the prosthetic valve device 150. When the plurality of first attachment members 157 are manually pushed onto the inflow capture device 122 in sequential or consecutive order, the first attachment members 157 are released in reverse order from which they were loaded such that the last first attachment member 157 loaded onto the inflow capture device 122 is the first released from the inflow capture device 122. Thus, if the first attachment members 157 are loaded onto the inflow capture device 122 in the consecutive order of 157A, 157B, 157C, 157D, 157E, 157F, they would be released from the inflow capture device 122 in the reverse consecutive order of 157F, 157E, 157D, 157C, 157B, 157A. In an embodiment, all of the first attachment members 157 are consecutively loaded onto the inflow capture device 122 on a first winding 123A thereof (shown in FIG. 6B) such that they are released via a single full rotation of the inflow capture device 122.

Figure 6B:
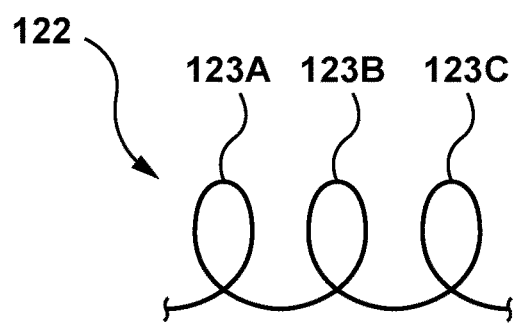
FIG. 6B is a side view of the inflow capture device of the delivery system of FIG. 2, wherein the inflow capture device is a coil having a plurality of windings and the inflow capture device is shown removed from the delivery system for illustrative purposes only.

In another embodiment of loading the inflow end 156 of the prosthetic valve device 150, the plurality of first attachment members 157 are manually pushed one-by-one along the loading rail 540, then onto the inflow capture device 122, in non-consecutive order. When the first attachment members 157 are loaded onto the inflow capture device 122 in non-consecutive order, adjacent first attachment members 157 are staggered or spaced apart from each other when released from the inflow capture device 122. More particularly, the total number of first attachment members 157 may be considered to include a first set of first attachment members that includes, for example, 157A, 157C, 157E and a second set of first attachment members that includes, for example, 157B, 157D, 157F. As shown in FIG. 6B, which is a side view of the inflow capture device 122 removed from the delivery system 100 for illustrative purposes, the inflow capture device 122 has a plurality of windings 123A, 123B, 123C. When loaded onto the inflow capture device 122, the first set of first attachment members 157A, 157C, 157E are loaded onto the second winding 123B and then the second set of first attachment members 157B, 157D, 157F are loaded onto the first winding 123A. The first attachment members 157 are released from the inflow capture device 122 by two complete rotations of the inflow capture device 122, with the first complete rotation releasing the second set of first attachment members 157B, 157D, 157F and the second complete rotation releasing the first set of first attachment members 157A, 157C, 157E. In this manner, only a subset of the total first attachment members (i.e., the second set of first attachment members 157B, 157D, 157F) are released with the first complete rotation. The endmost crowns 151A attached to the second set of first attachment members 157B, 157D, 157F are thus permitted to self-center in the anatomy prior to releasing the endmost crowns 151A attached to the remaining first attachment members. When the first set of first attachment members 156A, 157C, 157E are then released with a second complete rotation, the endmost crowns 151A attached thereto are distributed equally between the endmost crowns 151A of the prosthetic valve device 150 that have already been released. This staggered or non-consecutive release of the endmost crowns 151A results in more uniform crown spacing than the spacing that results from consecutive loading and release of the first attachment members 157. Uniform crown spacing is beneficial to prevent paravalvular leakage and migration, and further provides optimal structural integrity performance.

As described above, each first attachment member of the first set of first attachment members 157A, 157C, 157E is disposed between two adjacent first attachment members of the second set of first attachment members 157B, 157D, 157F. However, different non-consecutive order combinations of the first attachment members may be utilized when loading the first attachment members 157 onto the inflow capture device 122. Stated another way, although described above that the total number of first attachment members 157 may be considered to include a first set of first attachment members that includes 157A, 157C, 157E and a second set of first attachment members that includes 157B, 157D, 157F, other non-consecutive order sets of attachment members are contemplated. For example, in another embodiment, the total number of first attachment members 157 may be considered to include a first set of first attachment members that includes 157B, 157C, 157E, 157F and a second set of first attachment members that includes 157A, 157D. In this example, each first attachment member of the first set of first attachment members is disposed adjacent to at least one first attachment member of the second set of first attachment members. In an embodiment, at least two first attachment members of the first set of first attachment members are disposed directly adjacent to at least one first attachment member of the second set of first attachment members. In another example, the total number of first attachment members 157 may be considered to include a first set of first attachment members that includes 157A, 157C, a second set of first attachment members that includes 157E, 157B, and a third set of first attachment members that includes 157D, 157F. The first set of attachment members 157A, 157C are loaded onto the third winding 123C, the second set of attachment members 157E, 157B are loaded onto the second winding 123B, and the third set of attachment members 157D, 157F are loaded onto the first winding 123A, and three complete rotations of the inflow capture device 122 are required to release all of the first attachment members 157. Many various non-consecutive order combinations may be utilized to deploy the endmost crowns 151A in a staggered or non-consecutive manner for more uniform spacing therebetween.

Figure 6C:
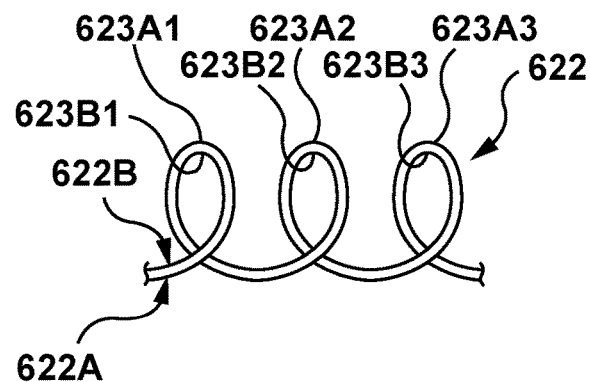
FIG. 6C is a side view of an inflow capture device according to another embodiment hereof, wherein the inflow capture device includes an outer coil having a plurality of windings and an inner coil having a plurality of windings and the inflow capture device is shown removed from the delivery system for illustrative purposes only.

In another embodiment hereof, the inflow capture device may include a double or dual coil to achieve staggered deployment of the endmost crowns 151A. More particularly, with reference to FIG. 6C, an inflow capture device 622 includes an outer coil 622A including a plurality of windings 623A1, 623A2, 623A3 and an inner coil 622B including a plurality of windings 623B1, 623B2, 623B3. The inner coil 622B is radially disposed within the outer coil 622A. When the first attachment members 157 are loaded onto the inflow capture device 622, opposing pairs of first attachment members 157 may be loaded onto corresponding windings of the outer and inner coils 622A, 622B such that the opposing pair of first attachment members 157 are configured to deploy from the inflow capture device 622 at the same time. For example, the total number of first attachment members 157 may be considered to include a first set of first attachment members that includes, for example, opposing pair of first attachment members 157A, 157D, a second set of first attachment members that includes, for example, opposing pair of first attachment members 157B, 157E, and a third set of first attachment members that includes, for example, opposing pair of first attachment members 157C, 157F. When loaded, the first set of first attachment members 157A, 157D are loaded onto the inflow capture device 622 with first attachment member 157A being loaded onto winding 623A3 of the outer coil 622A and first attachment member 157D being loaded onto corresponding winding 623B3 of the inner coil 622B. Similarly, the second set of first attachment members 157B, 157E are loaded onto the inflow capture device 622 with first attachment member 157B being loaded onto winding 623A2 of the outer coil 622A and first attachment member 157E being loaded onto corresponding winding 623B2 of the inner coil 622B. Lastly, the third set of first attachment members 157C, 157F are loaded onto the inflow capture device 622 with first attachment member 157C being loaded onto winding 623A1 of the outer coil 622A and first attachment member 157F being loaded onto corresponding winding 623B1 of the inner coil 622B. In this embodiment, the first attachment members 157 are released from the inflow capture device 622 by three complete rotations of the inflow capture device 622, with the first complete rotation releasing the third set of first attachment members 157C, 157F, the second complete rotation releasing the second set of first attachment members 157B, 157E, and the third complete rotation releasing the third set of first attachment members 157A, 157D. In this manner, only a subset of the total first attachment members are released with each complete rotation and each subset is an opposing pair of first attachment members. The endmost crowns 151A attached to each opposing pair of first attachment members are thus permitted to self-center in the anatomy prior to releasing the endmost crowns 151A attached to the remaining first attachment members. When the last opposing pair of first attachment members are then released, the endmost crowns 151A attached thereto are distributed equally between the endmost crowns 151A of the prosthetic valve device 150 that have already been released. This staggered or non-consecutive release of the endmost crowns 151A results in more uniform crown spacing than the spacing that results from consecutive loading and release of the first attachment members 157. Uniform crown spacing is beneficial to prevent paravalvular leakage and migration, and further provides optimal structural integrity performance.

Figure 7:
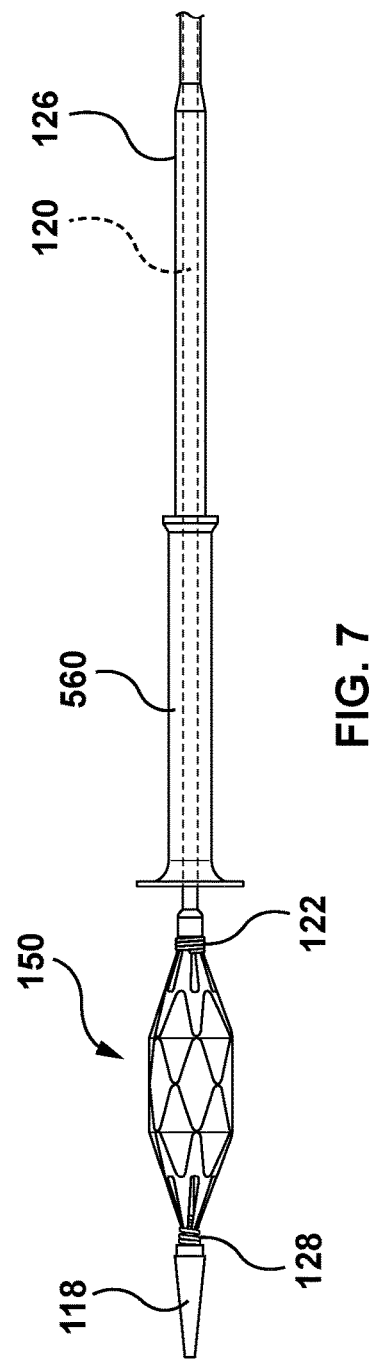
FIG. 7 is a side perspective view of the delivery system of FIG. 2 and the prosthetic valve device of FIG. 1 with the inflow capture device of the delivery system engaged or attached to the inflow end of the prosthetic valve device and the outflow capture device of the delivery system engaged or attached to the outflow end of the prosthetic valve device.

After the inflow end 156 of the prosthetic valve device 150 is coupled to the inflow capture device 122, the outflow end 158 of the prosthetic valve device 150 is coupled to the outflow capture device 128 as shown in FIG. 7. FIG. 7 is a side perspective view of the delivery system 100 with the inflow capture device 122 of the delivery system 100 engaged or attached to the inflow end 156 of the prosthetic valve device 150 and the outflow capture device 128 of the delivery system 100 engaged or attached to the outflow end 158 of the prosthetic valve device 150. Loading the outflow end 158 to the outflow capture device 128 is similar to loading the inflow end 156 to the inflow capture device 122. The loading rail 540 (not shown in FIG. 7) is inserted or threaded through the plurality of second attachment members 159 on the outflow end 158 of the prosthetic valve device 150. Once the loading rail 540 is connected to the outflow capture device 128, the plurality of second attachment members 159 are each manually pushed one-by-one along the loading rail 540, then onto the outflow capture device 128. As the second attachment members 159 are pushed along and onto the outflow capture device 128, the outflow end 158 of the prosthetic valve device 150 is compressed or collapsed. Once all of the second attachment members 159 are pushed off the loading rail 540 and are loaded onto the outflow capture device 128, the loading rail 540 is removed from the outflow capture device 128. FIG. 7 shows the outflow end 158 of the prosthetic valve device 150 connected to the outflow capture device 128 as described, with the outflow end 158 of the of the prosthetic valve device 150 being compressed to closely match the diameter of the outflow capture device 128.

Similar to the embodiments described above for the inflow end 156, the plurality of second attachment members 159 may be manually pushed one-by-one along the loading rail 540, then onto the outflow capture device 128, in consecutive or non-consecutive order. In an embodiment, all of the second attachment members 159 are sequentially or consecutively loaded onto the outflow capture device 128 on a first winding thereof such that they are released via a single full rotation of the outflow capture device 128. In another embodiment of loading the outflow end 158 of the prosthetic valve device 150, the plurality of second attachment members 159 are manually pushed one-by-one along the loading rail 540, then onto the outflow capture device 128, in non-consecutive order. More particularly, the total number of second attachment members 159 may be considered to include a first set of second attachment members and a second set of second attachment members. When loaded onto the outflow capture device 128, the first set of second attachment members are loaded onto a second winding of the outflow capture device 128 and then the second set of second attachment members are loaded onto a first winding of outflow capture device 128. The second attachment members 159 are released from the outflow capture device 128 by two complete rotations of the outflow capture device 128, with the first complete rotation releasing the second set of second attachment members and the second complete rotation releasing the first set of second attachment members. In this manner, only a subset of the second attachment members 159 are released with the first complete rotation and the initially-released endmost crowns 151B of the prosthetic valve device 150 are permitted to self-center in the anatomy prior to releasing the remaining attachment members. When the endmost crowns 151B attached to the first set of second attachment members are released with a second complete rotation, they are distributed equally between the endmost crowns of the prosthetic valve device that have already been released. This staggered or non-consecutive release of the endmost crowns 151B results in more uniform crown spacing than the spacing that results from consecutive loading and release of the second attachment members. Various non-consecutive order combinations of the second attachment members 159 may be utilized when loading the second attachment members 159 onto the outflow capture device 128. In an embodiment, each second attachment member of the first set of second attachment members is disposed between two adjacent second attachment members of the second set of second attachment members. In another embodiment, each second attachment member of the first set of second attachment members is disposed adjacent to at least one second attachment member of the second set of second attachment members. In another embodiment, at least two second attachment members of the first set of second attachment members are disposed directly adjacent to at least one second attachment member of the second set of second attachment members. In another embodiment, the outflow capture device 128 may be a double or dual coil similar to the inflow capture device 622 shown in FIG. 6C, and opposing pairs of the second attachment members may be loaded onto corresponding windings of the outer and inner coils thereof for staggered release of the endmost crowns. Many various non-consecutive order combinations may be utilized to deploy the endmost crowns in a staggered manner for more uniform spacing therebetween.

Although the method of loading described herein includes attaching the inflow end 156 of the prosthetic valve device 150 to the delivery system 100 prior to attaching the outflow end 158 of the prosthetic valve device 150 to the delivery system, the order may be reversed and the outflow end 158 may be attached prior to the inflow end 156.

Figure 8:
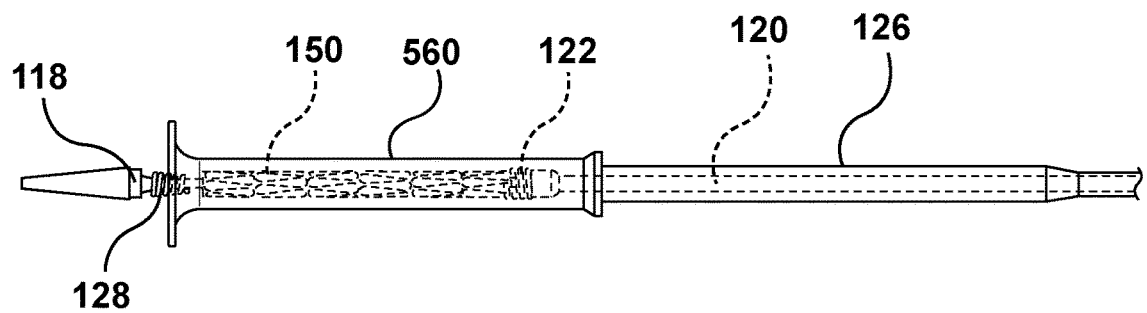
FIG. 8 is a side perspective view of the delivery system of FIG. 2 and the prosthetic valve device of FIG. 1 as the prosthetic valve device is being collapsed and retracted into a loading funnel.

After both the inflow and outflow ends 156, 158 of the prosthetic valve device 150 are attached to the delivery system 100, a loading funnel 560 is used to further compress the prosthetic valve device 150 for eventual enclosure in the delivery system 100. The loading funnel 560 is loaded onto the delivery system 100 from the proximal end 104 of the delivery system 100 to a location as shown in FIGS. 5-7. After both the inflow and outflow ends 156, 158 of the prosthetic valve device 150 are coupled to delivery system as shown in FIG. 7, the loading funnel 560 may be advanced distally causing the prosthetic valve device 150 to be compressed by advancement of the loading funnel 560. Alternatively, the assembly of the outer shaft 120, the inner shaft 114, and the prosthetic valve device 150 may be retracted proximally into the loading funnel 560. FIG. 8 is a side perspective view of the delivery system 100 with the prosthetic valve device 150 completely collapsed or enclosed within the loading funnel 560.

Figure 9:
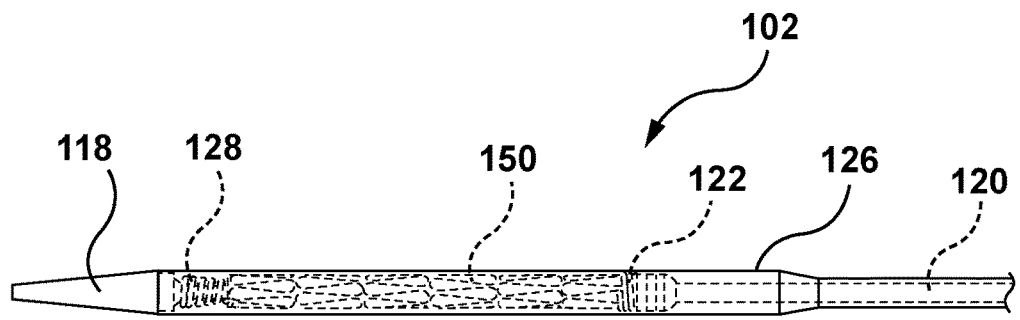
FIG. 9 is a side perspective view of the delivery system of FIG. 2 and the prosthetic valve device of FIG. 1 in which the prosthetic valve device is enclosed in a retractable sheath of the delivery system in a radially compressed configuration and is ready for intraluminal insertion or delivery to a desired anatomic site.

The assembly of the outer shaft 120, the inner shaft 114, and the prosthetic valve device 150 may be further retracted proximally until the collapsed prosthetic valve device 150 is disposed within the retractable sheath 126 and the distal tip 118 fits into the distal end of the retractable sheath 126 as shown in FIG. 9. FIG. 9 shows the distal end 102 of the delivery system 100 as it can be inserted intraluminally to a desired anatomic site for delivery of the prosthetic valve device 150. At this point, the retractable sheath 126 contains the collapsed prosthetic valve device 150 in order to compress the prosthetic valve device 150 to have a profile reduced enough to be inserted into a desired anatomic site and to provide a smooth profile for insertion. The loading funnel 560 has been removed from the delivery system 100 by distally advancing the loading funnel 560 until it is removed from the delivery system 100.

Figure 10:
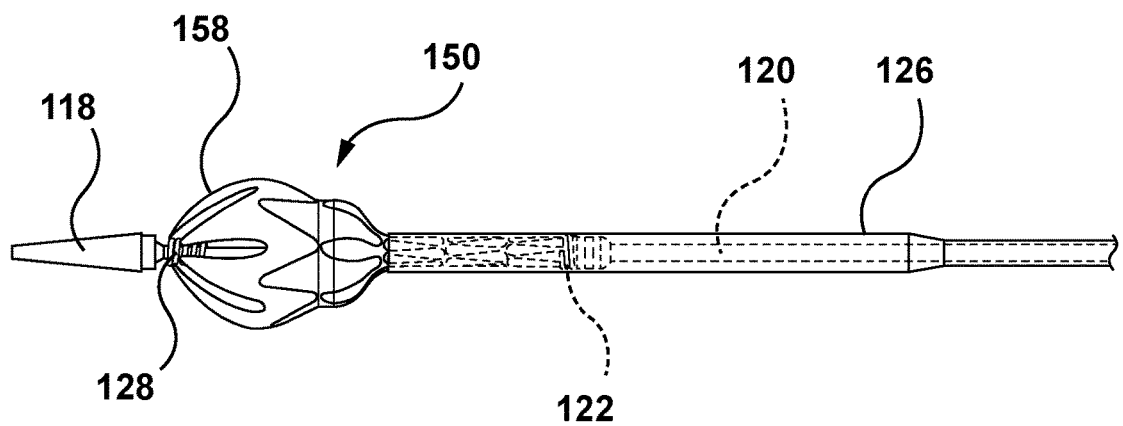
FIG. 10 is a side perspective view of the delivery system of FIG. 2 and the prosthetic valve device of FIG. 1 in which the retractable sheath is partially retracted and the prosthetic valve device is partially expanded during deployment thereof, wherein the outflow capture device of the delivery system is still engaged or attached to the outflow end of the prosthetic valve device.

In order to deploy or release the prosthetic valve device 150 once it has been positioned at its desired location in situ in the vasculature or in a heart valve annulus, for example, the retractable sheath 126 is either retracted proximally, or the assembly of the outer shaft 120, the inner shaft 114, and the prosthetic valve device 150 is pushed out the distal end of the retractable sheath 126. Notably, the pushability of the assembly of the outer shaft 120, the inner shaft 114, and the prosthetic valve device 150 is improved with both the inflow and outflow ends of the prosthetic valve device 150 being constrained by the inflow and outflow capture devices 122, 128 because such constraint prevents any inadvertent buckling of the prosthetic valve device 150 that may otherwise occur when being pushed in a distal direction without both the inflow and outflow ends of the prosthetic valve device 150 being constrained by the inflow and outflow capture devices 122, 128. In FIG. 10, deployment of the prosthetic valve device 150 is initiated via retraction of the retractable sheath 126. FIG. 10 is a side perspective view of the delivery system 100 in which the retractable sheath 126 is partially retracted to expose at least the distal end 158 of the prosthetic valve device 150 and the exposed length of the prosthetic valve device 150 is partially expanded. The outflow end 158 of the prosthetic valve device 150 is still engaged or attached to the outflow capture device 128 of the delivery system 100. Although the retractable sheath 126 is shown as only partially retracted, an operator may retract the retractable sheath 126 to expose the entire length of the prosthetic valve device 150. At this stage of deployment, positioning of the delivery system 100 may still be adjusted and/or the retractable sheath 126 may be distally advanced to recapture the prosthetic valve device 150. The inner shaft 114 having the outflow capture device 128 attached thereto, and the outer shaft 120 having the inflow capture device 122 attached thereto, may be independently moved or translated in a longitudinal or axial direction in order to assist in deployment and/or positioning of the prosthetic valve device 150. More particularly, even if the retractable sheath 126 is retracted to expose the entire length of the prosthetic valve device 150, the prosthetic valve device 150 may essentially be stretched or tensioned via translation of the proximal and/or outflow capture devices 122, 128. Since the prosthetic valve device 150 may be stretched or tensioned, the profile thereof may be sufficiently reduced to enable to the retractable sheath 126 to be distally advanced to recapture the prosthetic valve device 150 and thus allow repositioning thereof in situ.

Figure 11:
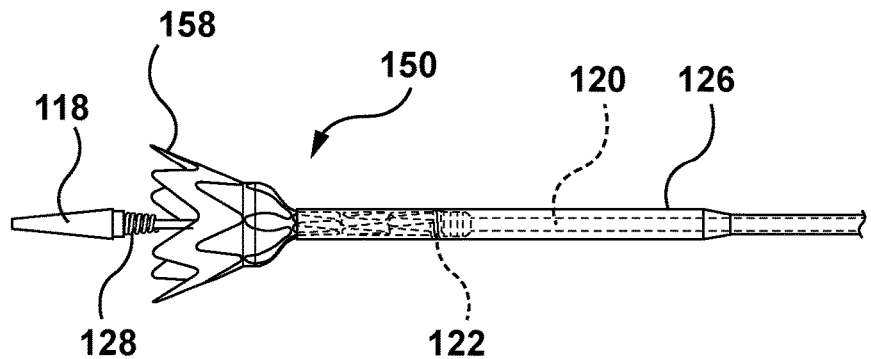
FIG. 11 is a side perspective view of the delivery system of FIG. 2 and the prosthetic valve device of FIG. 1 in which the retractable sheath is partially retracted and the prosthetic valve device is partially expanded during deployment thereof, wherein the outflow end of the prosthetic valve device is fully deployed and is no longer engaged or attached to the outflow capture device of the delivery system.

In FIG. 11, the outflow end 158 of the prosthetic valve device 150 is released from the outflow capture device 128 and permitted to self-expand. More particularly, the outflow capture device 128 is rotated until the plurality of second attachment members 159 are all released from the windings of the outflow capture device 128. As described above, the outflow capture device 128 is rotated via rotation of the inner shaft 114, which is independently rotated relative to the other components of the delivery system 100 by rotating or turning the handle 113 to which it is attached.

Figure 12:
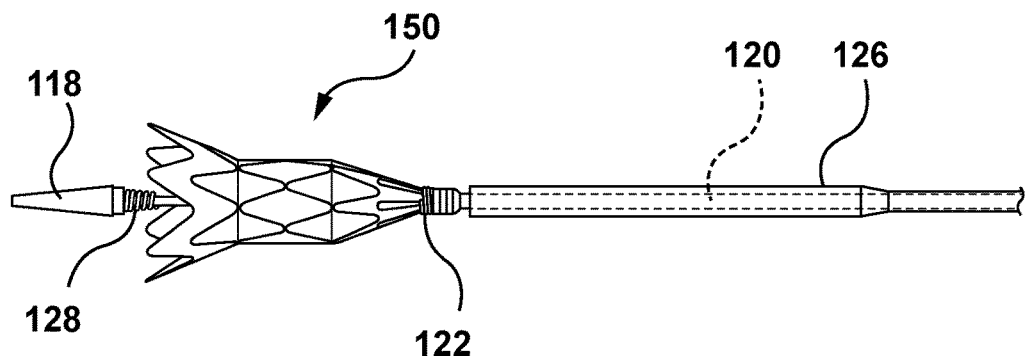
FIG. 12 is a side perspective view of the delivery system of FIG. 2 and the prosthetic valve device of FIG. 1 in which the retractable sheath is retracted to expose an entire length of the prosthetic valve device and the prosthetic valve device is partially expanded during deployment thereof, wherein the outflow end of the prosthetic valve device is fully deployed and is no longer engaged or attached to the outflow capture device of the delivery system and wherein the inflow capture device of the delivery system is still engaged or attached to the inflow end of the prosthetic valve device.

In FIG. 12, the retractable sheath 126 is fully retracted to expose an entire length of the prosthetic valve device 150, with the inflow end 156 of the prosthetic valve device 150 still engaged or attached to the inflow capture device 122 of the delivery system 100. However, as stated above, the retractable sheath 126 may have been fully retracted to expose an entire length of the prosthetic valve device 150 prior to releasing the outflow end 158 of the prosthetic valve device 150 from the outflow capture device 128.

Figure 13:
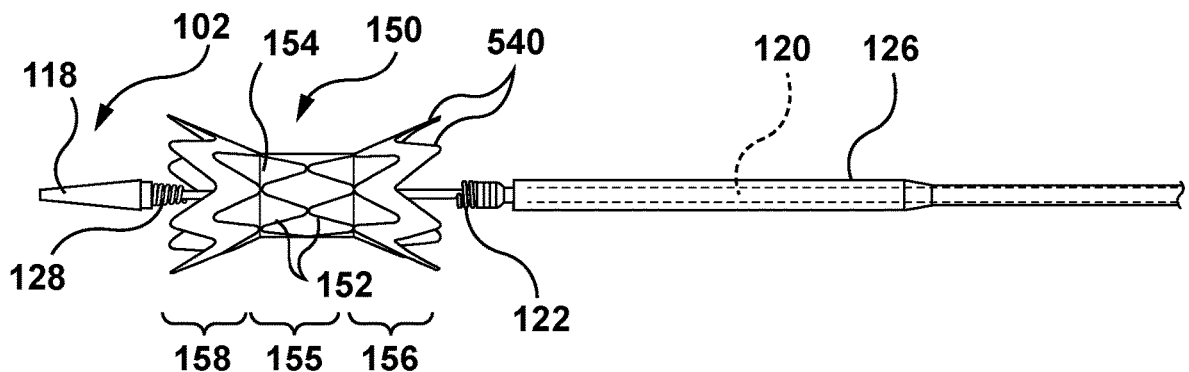
FIG. 13 is a side perspective view of the delivery system of FIG. 2 and the prosthetic valve device of FIG. 1 in which the prosthetic valve device is fully expanded or deployed and released from the delivery system, wherein the inflow and outflow ends of the prosthetic valve device are fully deployed and are no longer engaged or attached to the inflow and outflow capture devices, respectively, of the delivery system.

In FIG. 13, the inflow end 156 of the prosthetic valve device 150 is released from the inflow capture device 122 and permitted to self-expand. FIG. 13 is a side perspective view of the delivery system 100 in which the prosthetic valve device 150 is fully expanded or deployed and released from the delivery system 100, wherein the inflow and outflow ends 156, 158 of the prosthetic valve device 150 are no longer engaged or attached to the inflow and outflow capture devices 122, 128, respectively, of the delivery system 100. More particularly, in order to fully release the prosthetic valve device 150 from the delivery system 100, the inflow capture device 122 is rotated until the plurality of first attachment members 157 are all released from the windings of the inflow capture device 122. As described above, the inflow capture device 122 is rotated via rotation of the outer shaft 120, which is independently rotated relative to the other components of the delivery system 100 via the second rotating homeostasis valve 110 to which it is attached. Advantageously, blood can flow through the delivery system 100 at this point, thereby maintaining relatively normal heart function during the procedure. Once the prosthetic valve device 150 is released from the delivery system 100, the delivery system 100 may be removed from the patient.

In an embodiment, after the prosthetic valve device 150 is released from the delivery system 100, the user may move the inner shaft 114 and the outer shaft 120 relative to each other in order lock or join the coils of the proximal and outflow capture devices 122, 128 together prior to removing the delivery system 100 from the patient. Locking or joining the coils of the proximal and outflow capture devices 122, 128 together prior to removing the delivery system 100 from the patient may reduce inadvertent damage to the anatomy during removal.

Figure 14:
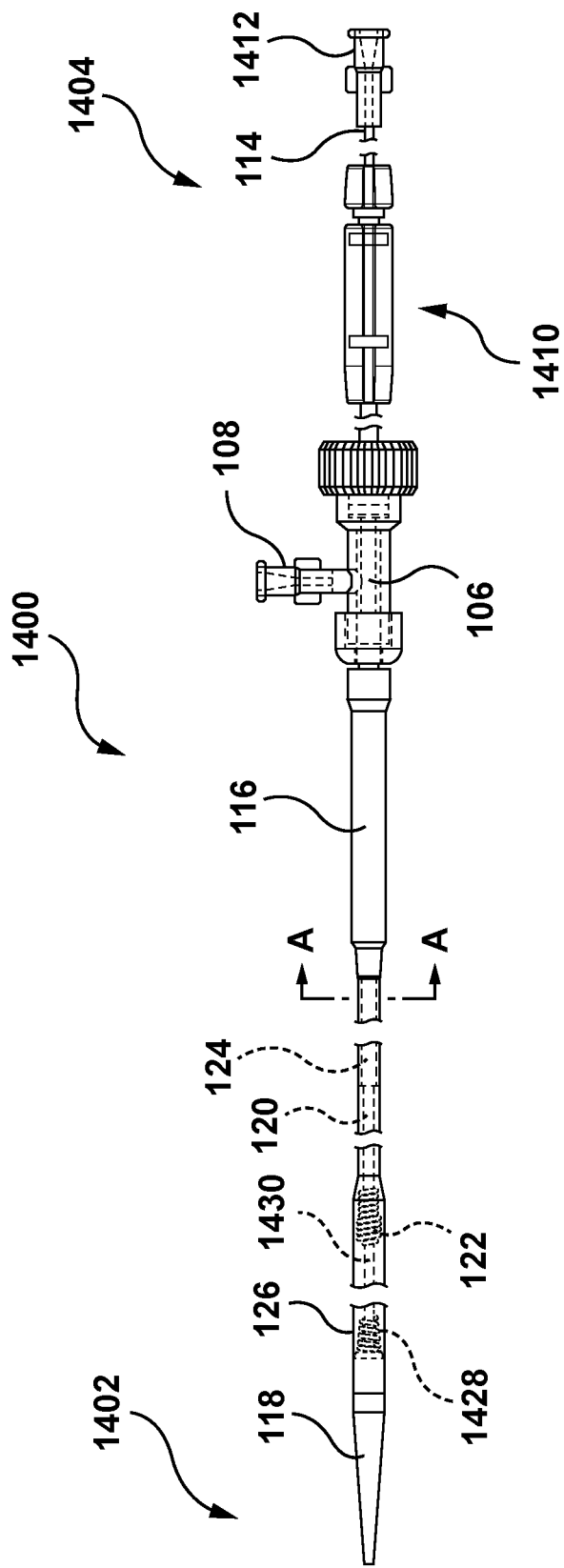
FIG. 14 is a side view of a delivery system according to an embodiment hereof, wherein the delivery system includes an inflow capture device configured to engage an inflow end of a prosthetic valve device and an outflow capture device configured to engage an outflow end of the prosthetic valve device when the prosthetic valve device is loaded within the delivery system.

FIG. 14 is a side view of a delivery system 1400 according to another embodiment hereof. The delivery system 1400 is configured to receive the prosthetic valve device 150 and percutaneously deliver the prosthetic valve device 150 in a compressed configuration to a treatment site in situ. More particularly, similar to the delivery system 100, the delivery system 1400 includes the inflow capture device 122 configured to engage or attach to the plurality of first attachment members 157 on or near the inflow end 156 of the prosthetic valve device 150 and an outflow capture device 1428 configured to engage or attach to the plurality of second attachment members 159 on or near the outflow end 158 of the prosthetic valve device 150. In the embodiment of FIGS. 14-18, the outflow capture device 1428 includes a coil 1428A configured for engagement through openings in the plurality of second attachment members 159 that is rotatable to release the plurality of second attachment members 159 and the inflow capture device 122 is also a coil configured for engagement through openings in the plurality of first attachment members 157 that is rotatable to release the plurality of first attachment members 157. However, unlike the outflow capture device 128 of the delivery system 100, the outflow capture device 1428 is disposed on an intermediate shaft 1430 that is disposed between the inner shaft 114 and the outer shaft 120. The intermediate shaft 1430, and the outflow capture device 1428 attached thereto, is rotatable relative to the inner shaft 114 such that the inner shaft 114 (and the distal tip 118 attached thereto) is not required to rotate in order to release the plurality of second attachment members 159 from the outflow capture device 1428.

The delivery system 1400 includes a distal end generally designated by the reference numeral 1402 and a proximal end generally designated by the reference number 1404. The proximal end 1404 of the delivery system 1400 remains outside of the patient, and the distal end 1402 is inserted into the patient and is delivered intravascularly to an area at or near a pulmonary valve inside the body. Other uses for the delivery system 1400 in other areas of the body, however, are also contemplated. The proximal end 1404 includes means for remotely controlling the distal end 1402 of the delivery system 1400, in particular relating to deploying or releasing the prosthetic valve device 150 from the delivery system 1400 in situ.

The components of the proximal end 1404 of the delivery system 1400 may include those shown in FIG. 14, although additional and/or alternative components are also contemplated. FIG. 14 includes the first rotating homeostasis valve 106 previously described with respect to the delivery system 100, the side access port 108 previously described with respect to the delivery system 100, and a handle 1410 previously described with respect to the delivery system 100. The handle 1410 controls the components of the distal end 1402 as described in more detail below by independent rotation of two portions of the handle 1410. The proximal end 1404 of the delivery system 1400 includes a guidewire inlet 1412, which is described in more detail below. The components of the proximal end 1404 of the delivery system 1400 are exemplary. Other alternative or additional components of the proximal end 1404 of the delivery system 1400 are also contemplated by the invention.

Figure 14A:
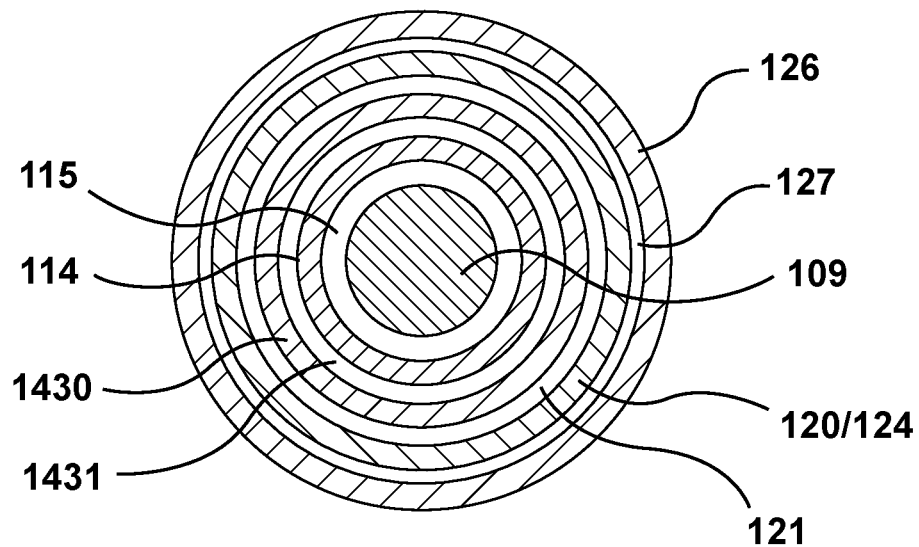
FIG. 14A is a cross-sectional view of the delivery system of FIG. 14 taken along line A-A of FIG. 14.

FIG. 14 shows the distal end 1402 of the delivery system 1400 in an assembled configuration, without a prosthetic valve device attached or loaded thereto. FIG. 14A is a cross-sectional view of the delivery system of FIG. 14 taken along line A-A of FIG. 14. As best shown on FIG. 14A, the delivery system 1400 includes at least four concentric tubular components. More particularly, the delivery system 1400 includes the inner shaft 114 which defines the guidewire lumen 115, the intermediate shaft 1430 which defines a lumen 1431 and is slidingly disposed over the inner shaft 114, the outer shaft 120 which defines the lumen 121 and is slidingly disposed over the intermediate shaft 1430, and the retractable sheath 126 which defines the lumen 127 and is slidingly disposed over the outer shaft 120 to hold the prosthetic valve device 150 in a radially collapsed or compressed configuration during delivery. The delivery system 1400 may further include the outer sleeve 116 that is disposed over a proximal portion of the retractable sheath 126 to keep blood from leaking back around the delivery system 1400.

The inner shaft 114, as previously described with respect to the delivery system 100, includes the tapered distal tip 118 attached thereto at its distal end and is attached to the guidewire lumen inlet 1412 at its proximal end such that the inner shaft 114 may be tracked over the guidewire 109. Inner shaft 114 may be independently advanced or retracted through other components of the delivery system 1400 by moving the guidewire lumen inlet 1412 to which it is attached.

The intermediate shaft 1430 is slidingly disposed over the inner shaft 114 and is independently rotatable with respect to the other shaft components of the delivery system 1420. The intermediate shaft 1430 may be formed of one or more polymeric materials, non-exhaustive examples of which include polyethylene, polyethylene block amide copolymer (PEBA), polyamide and/or combinations thereof, either laminated, blended or co-extruded. Optionally, the intermediate shaft 1430 may be formed as a composite having a reinforcement layer incorporated within a polymeric body in order to enhance strength and/or torque-ability. Suitable reinforcement layers include braiding, wire mesh layers, embedded axial wires, embedded helical or circumferential wires, hypotubes, and the like. In this embodiment, the outflow capture device 1428 is coupled to a distal end of the intermediate shaft 1430. When the intermediate shaft 1430 is rotated via the handle 1410 as will be described in more detail below, the intermediate shaft 1430 and the outflow capture device 1428 collectively rotate as an assembly. Thus, movement of the intermediate shaft 1430, as controlled by the handle 1410, controls movement or rotation of the outflow capture device 1428. The intermediate shaft 1430 is also configured to be independently moved or translated in a longitudinal or axial direction relative to the other shaft components of the delivery system 1400. In an embodiment, the delivery system 1400 is configured to permit the intermediate shaft 1430 to move or translate between 10-65 mm.

Figure 15:
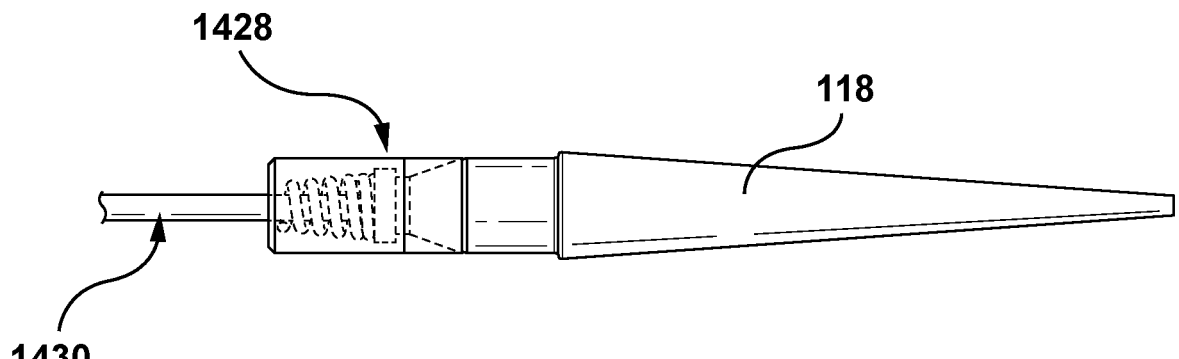
FIG. 15 is an enlarged side perspective view of a distal tip of the delivery system of FIG. 14.
Figure 16:
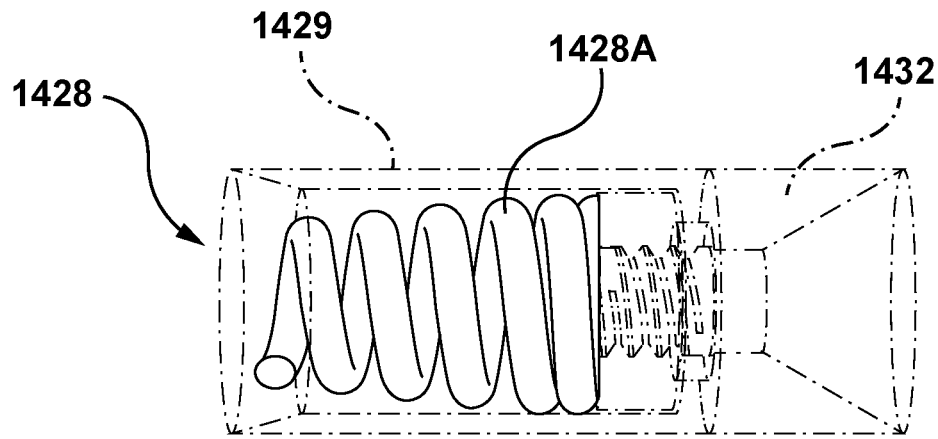
FIG. 16 is an enlarged side perspective view of the outflow capture device of the delivery system of FIG. 14, wherein the outflow capture device is shown removed from the delivery system for illustrative purposes only.

FIG. 15 is an enlarged side perspective view of the distal end of the delivery system 1400, while FIG. 16 is an enlarged side perspective view of the outflow capture device 1428 shown removed from the delivery system 1400 for illustrative purposes only. In this embodiment, the outflow capture device 1428 includes the coil 1428A including at least one complete winding about a longitudinal axis of the intermediate shaft 1430 and is configured for engagement through openings in the plurality of second attachment members 159. In an embodiment, the coil 1428A of the outflow capture device 1428 has an overall tapered profile with a distal end thereof having a larger diameter than a proximal end thereof. The outflow capture device 1428 also includes a hub 1432 attached to a distal end of the coil 1428. The hub 1432 is configured to attach to the intermediate shaft 1430 such that the outflow capture device 1428 moves and rotates with the intermediate shaft 1430 as an assembly. In an embodiment, the hub 1432 may include a plurality of threads on an inner surface thereof and the distal end of the intermediate shaft 1430 may include mating threads on an outer surface thereof such that the hub 1432 and the intermediate shaft 1430 may have a threaded relationship. However, a threaded relationship is not required and the hub 132 and the intermediate shaft 1430 may be coupled together via bonding or other suitable attachment mechanism. The hub 1432 is configured to abut against a proximal end of the distal tip 118 as shown in FIG. 15 such that there is a smooth transition between the two components. The outflow capture device 1428 may further include a relatively short polymeric sleeve 1429 attached to the distal end of the hub 1432. The polymeric sleeve 1429 extends in a proximal direction to cover the coil 1428A of the outflow capture device 1428. The polymeric sleeve 1429 is disposed over an outer surface of the coil 1428A in order to isolate the coil 1428A from the anatomy in situ after the outflow end 158 of the prosthetic valve device 150 is deployed. The polymeric sleeve 1429 is formed from a flexible and soft material that can be rolled, flipped, or other moved distally to expose the coil 1428A when the prosthetic valve device 150 is loaded onto the delivery system. Only the proximal edge of the coil 1428A is exposed when loading second attachment members 159 thereon. The polymeric sleeve 1429 is configured to not impede the windings of the coil 1428A during loading and deployment.

The outer shaft 120, as previously described with respect to the delivery system 100, is slidingly disposed over the intermediate shaft 1430. Surrounding the outer shaft 120 is the reinforcement layer 124, which is attached or otherwise bonded to the outer shaft 120 and serves to reinforce the outer shaft 120. Movement of the outer shaft 120 is controlled by the handle 1410 at the proximal end 1404 of the delivery system 1400. A portion of the handle 1410 is rotated or otherwise manipulated in order to rotate the outer shaft 120 or move the outer shaft 120 proximally and distally as desired. The inflow capture device 122 is coupled to a distal end of the outer shaft 120. When the outer shaft 120 is rotated via the handle 1410, the outer shaft 120 and the inflow capture device 122 collectively rotate as an assembly. Thus, movement of the outer shaft 120, as controlled by the handle 1410, controls movement or rotation of the inflow capture device 122. In this embodiment, the inflow capture device 122 is a coil including at least one complete winding about a longitudinal axis of the outer shaft 120 and is configured for engagement through openings in the plurality of first attachment members 157.

The inflow and outflow capture devices 122, 1428 provides means for releasably attaching the prosthetic valve device 150 onto the delivery system 1400 by holding the inflow and outflow ends 156, 158, respectively, of the prosthetic valve device 150 on the delivery system 1400 during delivery. The inflow capture device 122 is configured to hold the inflow end 156 of the prosthetic valve device 150 by engaging through openings in the plurality of first attachment members 157, while the outflow capture device 1428 is configured to hold the outflow end 158 of the prosthetic valve device 150 by engaging through openings in the plurality of second attachment members 159. The inflow and outflow capture devices 122, 1428 are further configured to release the prosthetic valve device 150 from the delivery system 1400 in situ. The intermediate shaft 1430 is rotatable in order to release the plurality of second attachment members 159. Stated another way, when the outflow capture device 1428 rotates or turns, the plurality of second attachment members 159 disengage or detach from the outflow capture device 1428, thus releasing the outflow end 158 of the prosthetic valve device 150. Similarly, the outer shaft 120 is rotatable in order to release the plurality of first attachment members 157. Stated another way, when the inflow capture device 122 rotates or turns, the plurality of first attachment members 157 disengage or detach from the inflow capture device 122, thus releasing the inflow end 156 of the prosthetic valve device 150. The speed that the inflow and outflow ends 156, 158 of the prosthetic valve device 150 are released from the delivery system 1400 are controlled by the rate of rotation of the inflow and outflow capture devices 122, 1428, respectively, therefore preventing uncontrolled release of the prosthetic valve device 150. The inflow and outflow ends 156, 158 of the prosthetic valve device 150 are selectively held, restrained, or otherwise controlled by the inflow and outflow capture devices 122, 1428, respectively, until the accurate positioning of the prosthetic valve device 150 is established. The coils of the inflow and outflow capture devices 122, 1428 have opposite winding directions such that the plurality of first attachment members 157 coupled to the inflow capture device 122 move in a distal direction along the coil winding(s) to release the inflow end 156 of the prosthetic valve device 150 while the plurality of second attachment members 159 coupled to the outflow capture device 1428 move in a proximal direction along the coil winding(s) to release the outflow end 158 of the prosthetic valve device 150.

Figure 17:
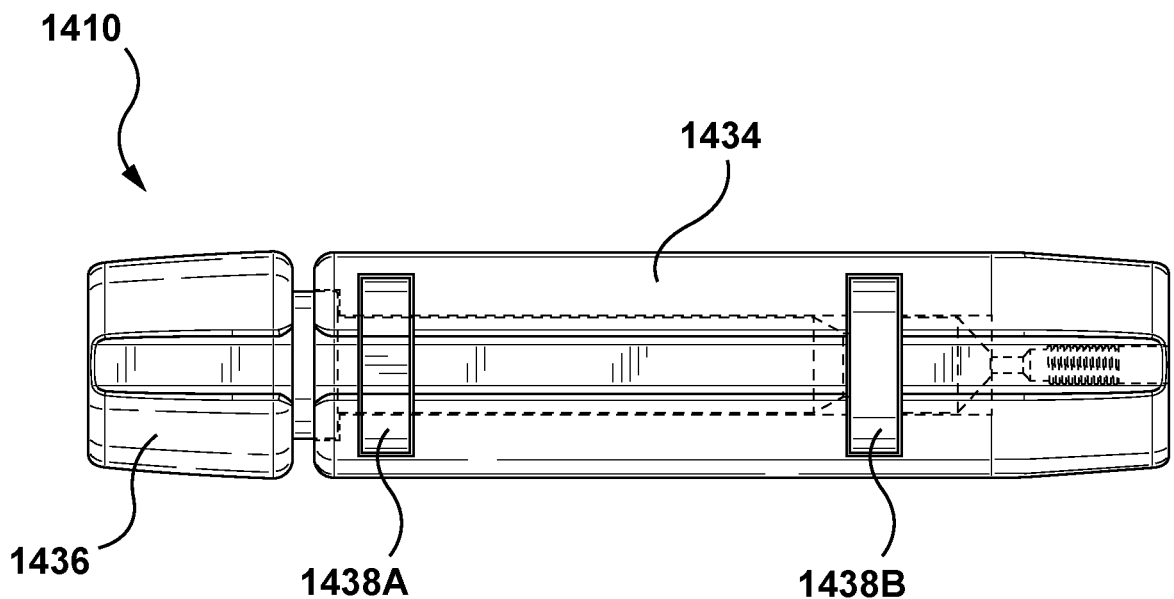
FIG. 17 is an enlarged top view of a handle of the delivery system of FIG. 14.
Figure 18:
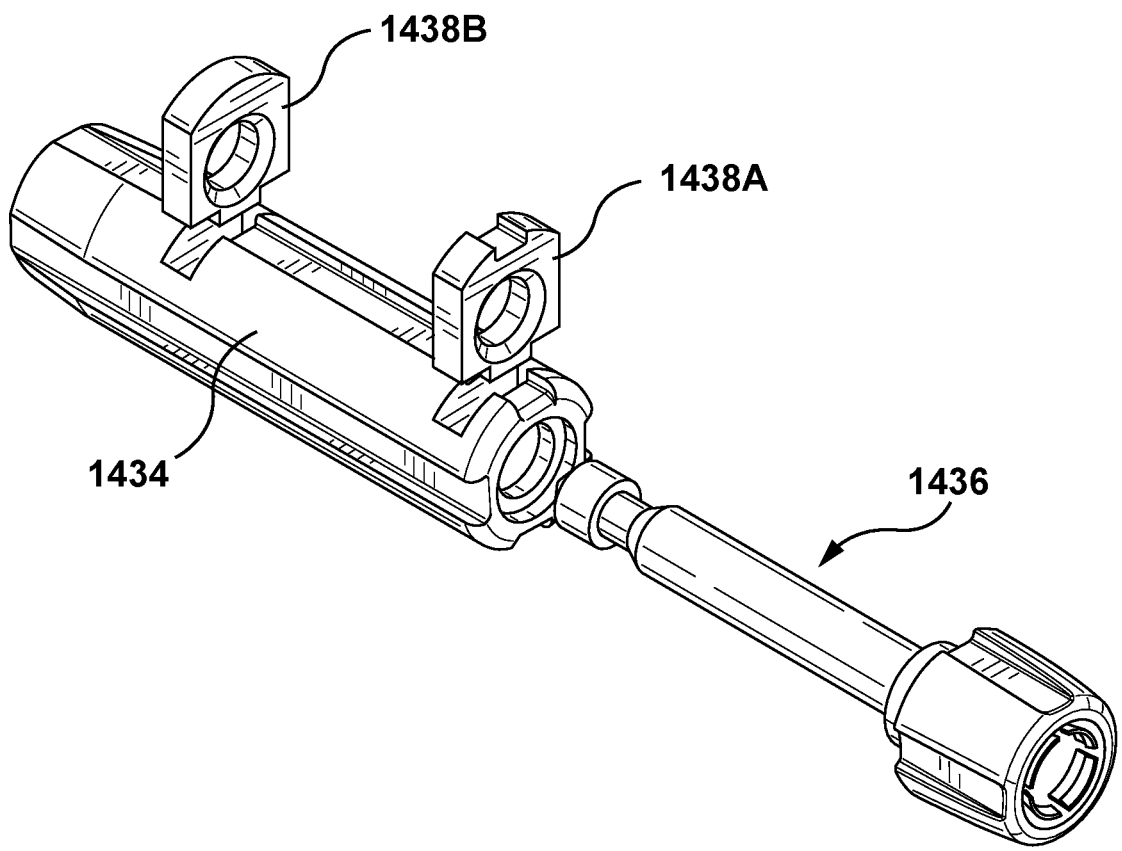
FIG. 18 is an exploded view of the handle of FIG. 17.

The handle 1410 is shown in a top view and an exploded view in FIGS. 17 and 18, respectively. The handle 1410 includes a female tuohy borst or rotating homeostasis valve 1434, a male tuohy borst or rotating homeostasis valve 1436, and two spring activated buttons 1438A, 1438B which hold or assemble the rotating homeostasis valves 1434, 1436 together. The male rotating homeostasis valve 1436 is coupled to a proximal end of the intermediate shaft 1430 such that when the male rotating homeostasis valve 1436 is rotated by a user, the intermediate shaft 1430 as well as the outflow capture device 1428 attached thereto rotates as well. In addition, the male rotating homeostasis valve 1436 may longitudinally translate or slide relative to the female rotating homeostasis valve 1434 such that the intermediate shaft 1430 as well as the outflow capture device 1428 attached thereto may be moved or translated in a longitudinal or axial direction relative to the remaining shaft components of the delivery system 1400. Thus, the male rotating homeostasis valve 1436 is rotated or otherwise manipulated in order to rotate the intermediate shaft 1430 or move the intermediate shaft 1430 proximally and distally as desired. A distal end of the male rotating homeostasis valve 1436 protrudes out of a distal end of the female rotating homeostasis valve 1434, and thus is accessible to the user to manipulate as desired. The male rotating homeostasis valve 1436 grips or forms a fluid seal around the intermediate shaft 1430 to prevent blood or other fluid from leaking back through the delivery system 1400. In addition, the male rotating homeostasis valve 1436 is configured to allow wires, devices and fluid to pass through.

The female rotating homeostasis valve 1434 is coupled to a proximal end of the outer shaft 120 such that when the female rotating homeostasis valve 1434 is rotated by a user, the outer shaft 120 as well as the inflow capture device 122 attached thereto rotates as well. In addition, the female rotating homeostasis valve 1434 may longitudinally translate or slide relative to the male rotating homeostasis valve 1436 such that the outer shaft 120 as well as the inflow capture device 122 attached thereto may be moved or translated in a longitudinal or axial direction relative to the remaining shaft components of the delivery system 1400. Thus, the female rotating homeostasis valve 1434 is rotated or otherwise manipulated in order to rotate the outer shaft 120 or move the outer shaft 120 proximally and distally as desired. The female rotating homeostasis valve 1434 is accessible to the user to manipulate as desired. The female rotating homeostasis valve 1434 grips or forms a fluid seal around the outer shaft 120 to prevent blood or other fluid from leaking back through the delivery system 1400.

The prosthetic valve device 150 is loaded onto the delivery system 1400 in the same manner as described above in FIGS. 5-9 with respect to the delivery system 100. In order to load or attach the prosthetic valve device 150 to each of the inflow and outflow capture devices 122, 1428 of the delivery system 1400, the loading rail 540 is utilized and subsequently removed. The first and second attachment members 157, 159 of the prosthetic valve device 150 may be loaded onto the respective capture device in a consecutive order or a non-consecutive order, as described above with respect to loading the prosthetic valve device 150 onto the delivery system 100. The loading funnel 560 is used to further compress the prosthetic valve device 150 for eventual enclosure in the delivery system 1400 and is subsequently removed after the prosthetic valve device 150 is retracted into the retractable sheath 126, as described above with respect to the delivery system 100 in FIGS. 8 and 9.

The prosthetic valve device 150 is deployed from the delivery system 1400 in a similar manner as described above in FIGS. 10-13 with respect to the delivery system 100. More particularly, in order to deploy or release the prosthetic valve device 150 once it has been positioned at its desired location in situ in the vasculature or in a heart valve annulus, for example, the retractable sheath 126 is either retracted proximally, or the assembly of the outer shaft 120, the intermediate shaft 1430, and the prosthetic valve device 150 is pushed out the end of the retractable sheath 126. Notably, the pushability of the assembly of the outer shaft 120, the intermediate shaft 1430, and the prosthetic valve device 150 is improved with both the inflow and outflow ends of the prosthetic valve device 150 being constrained by the inflow and outflow capture devices 122, 1428 because such constraint prevents any inadvertent buckling of the prosthetic valve device 150 that may otherwise occur when being pushed in a distal direction without both the inflow and outflow ends of the prosthetic valve device 150 being constrained by the inflow and outflow capture devices 122, 1428. The retractable sheath 126 is at least partially retracted to expose at least the outflow end 158 of the prosthetic valve device 150 and the prosthetic valve device 150 is partially expanded, with the outflow end 158 of the prosthetic valve device 150 still engaged or attached to the outflow capture device 1428 of the delivery system 1400. At this stage of deployment, positioning of the delivery system 1400 may still be adjusted and/or the retractable sheath 126 may be distally advanced to recapture the prosthetic valve device 150. The intermediate shaft 1430 having the outflow capture device 1428 attached thereto, and the outer shaft 120 having the inflow capture device 122 attached thereto, may be independently moved or translated in a longitudinal or axial direction in order to assist in deployment and/or positioning of the prosthetic valve device 150. More particularly, even if the retractable sheath 126 is retracted to expose the entire length of the prosthetic valve device 150, the prosthetic valve device 150 may essentially be stretched or tensioned via translation of the proximal and/or outflow capture devices 122, 1428. Since the prosthetic valve device 150 may be stretched or tensioned, the profile thereof may be sufficiently reduced to enable to the retractable sheath 126 to be distally advanced to recapture the prosthetic valve device 150 and thus allow repositioning thereof in situ.

The outflow end 158 of the prosthetic valve device 150 is then released from the outflow capture device 1428 and permitted to self-expand. More particularly, the outflow capture device 1428 is rotated until the plurality of second attachment members 159 are all released from the windings of the outflow capture device 1428. In this embodiment, the outflow capture device 1428 is rotated via rotation of the intermediate shaft 1430, which is independently rotated relative to the other shaft components of the delivery system 1400 via handle 1410.

The retractable sheath 126 is then fully retracted to expose an entire length of the prosthetic valve device 150, with the inflow end 156 of the prosthetic valve device 150 still engaged or attached to the inflow capture device 122 of the delivery system 1400. However, the retractable sheath 126 may have been fully retracted to expose an entire length of the prosthetic valve device 150 prior to releasing the outflow end 158 of the prosthetic valve device 150 from the outflow capture device 128.

The inflow end 156 of the prosthetic valve device 150 is then released from the inflow capture device 122 and permitted to self-expand. More particularly, in order to fully release the prosthetic valve device 150 from the delivery system 1400, the inflow capture device 122 is rotated until the plurality of first attachment members 157 are all released from the windings of the inflow capture device 122. As described above, the inflow capture device 122 is rotated via rotation of the outer shaft 120, which is independently rotated relative to the other shaft components of the delivery system 1400 via the handle 1410. Advantageously, blood can flow through the delivery system 1400 at this point, thereby maintaining relatively normal heart function during the procedure. Once the prosthetic valve device 150 is released from the delivery system 1400, the delivery system 1400 may be removed from the patient.

In an embodiment, after the prosthetic valve device 150 is released from the delivery system 1400, the user may move the intermediate shaft 1430 and the outer shaft 120 relative to each other in order lock or join the coils of the proximal and outflow capture devices 122, 1428 together prior to removing the delivery system 1400 from the patient. Locking or joining the coils of the proximal and outflow capture devices 122, 1428 together prior to removing the delivery system 1400 from the patient may reduce inadvertent damage to the anatomy during removal.

Figure 19:
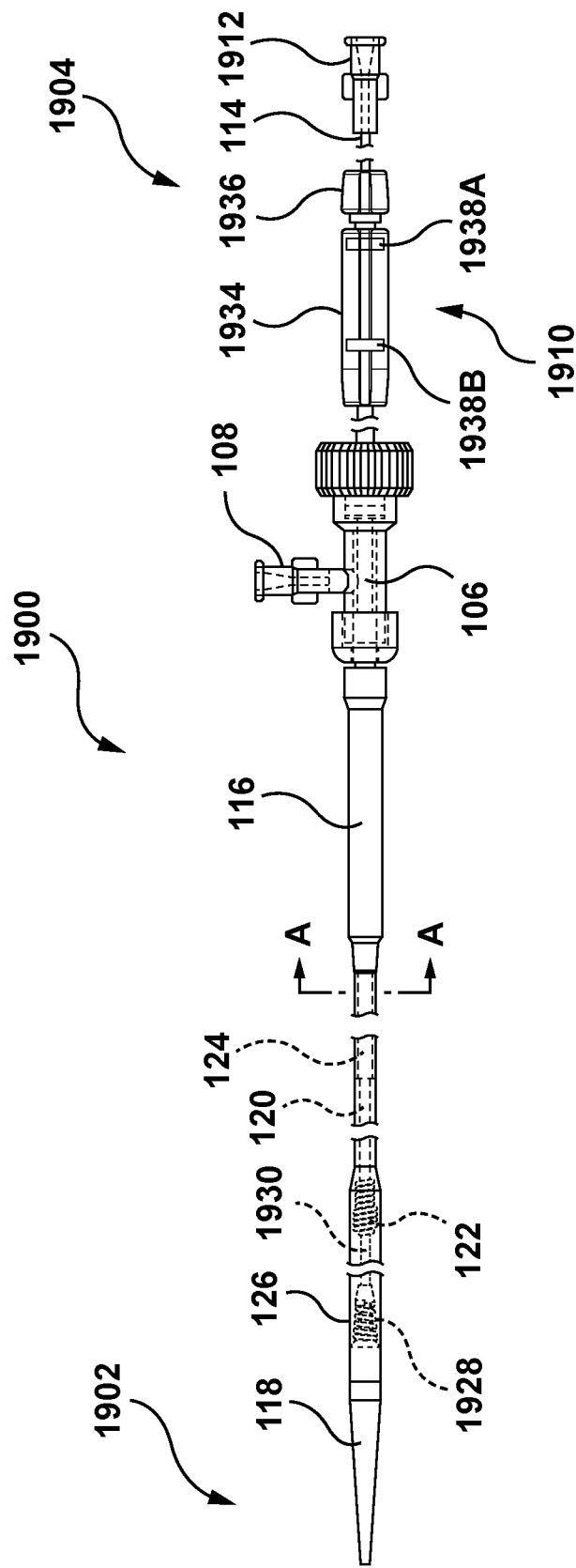
FIG. 19 is a side view of a delivery system according to an embodiment hereof, wherein the delivery system includes an inflow capture device configured to engage an inflow end of a prosthetic valve device and an outflow capture device configured to engage an outflow end of the prosthetic valve device when the prosthetic valve device is loaded within the delivery system.
Figure 20:
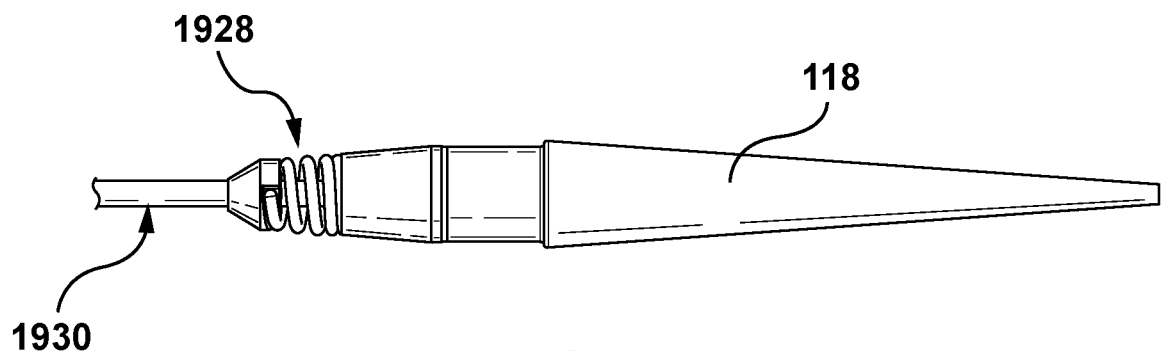
FIG. 20 is an enlarged side perspective view of a distal tip of the delivery system of FIG. 19.
Figure 21:
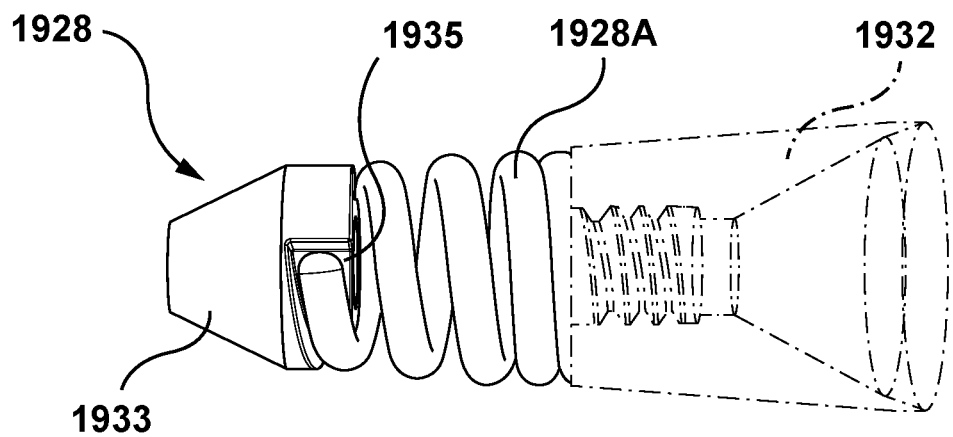
FIG. 21 is an enlarged side perspective view of the outflow capture device of the delivery system of FIG. 19, wherein the outflow capture device is shown removed from the delivery system for illustrative purposes only.

FIG. 19 is a side view of a delivery system 1900 according to another embodiment hereof. The delivery system 1900 is configured to receive the prosthetic valve device 150 and percutaneously deliver the prosthetic valve device 150 in a compressed configuration to a treatment site in situ. More particularly, similar to the delivery system 1400, the delivery system 1900 includes the inflow capture device 122 configured to engage or attach to the plurality of first attachment members 157 on or near the inflow end 156 of the prosthetic valve device 150 and an outflow capture device 1928 configured to engage or attach to the plurality of second attachment members 159 on or near the outflow end 158 of the prosthetic valve device 150. In the embodiment of FIGS. 19-21, the outflow capture device 1928 includes a coil 1928A configured for engagement through openings in the plurality of second attachment members 159 that is rotatable to release the plurality of second attachment members 159 and the inflow capture device 122 is also a coil configured for engagement through openings in the plurality of first attachment members 157 that is rotatable to release the plurality of first attachment members 157. Further, similar to the outflow capture device 1428 of the delivery system 1400, the outflow capture device 1928 is disposed on an intermediate shaft 1930 that is disposed between the inner shaft 114 and the outer shaft 120. Intermediate shaft 1930, and the outflow capture device 1928 attached thereto, are rotatable relative to the inner shaft 114 such that the inner shaft 114 (and the distal tip 118 attached thereto) is not required to rotate in order to release the plurality of second attachment members 159 from the outflow capture device 1928. However, in this embodiment, the outflow capture device 1928 has a different configuration than the outflow capture device 1428 of the delivery system 1400.

The delivery system 1900 includes a distal end generally designated by the reference numeral 1902 and a proximal end generally designated by the reference number 1904. The proximal end 1904 of the delivery system 1900 remains outside of the patient, and the distal end 1902 is inserted into the patient and is delivered intravascularly to an area at or near a pulmonary valve inside the body. Other uses for the delivery system 1900 in other areas of the body, however, are also contemplated. The proximal end 1904 includes means for remotely controlling the distal end 1902 of the delivery system 1900, in particular relating to deploying or releasing the prosthetic valve device 150 from the delivery system 1900 in situ.

The components of the proximal end 1904 of the delivery system 1900 may include those shown in FIG. 19, although additional and/or alternative components are also contemplated. FIG. 19 includes the first rotating homeostasis valve 106 previously described with respect to the delivery system 100, the side access port 108 previously described with respect to the delivery system 100, and a handle 1910 previously described with respect to the delivery system 100. The handle 1910 controls the components of the distal end 1902 as described in more detail below by independent rotation of two portions of the handle 1910. The handle 1910 is the same as the handle 1410 described above in FIGS. 17 and 18, and includes a female tuohy borst or rotating homeostasis valve 1934, a male tuohy borst or rotating homeostasis valve 1936, and two spring activated buttons 1938A, 1938B which hold or assemble the rotating homeostasis valves 1934, 1936 together. The female rotating homeostasis valve 1934 is rotated or otherwise manipulated in order to rotate the intermediate shaft 1930 (and outflow capture device 1928 attached thereto) or move the intermediate shaft 1930 (and outflow capture device 1928 attached thereto) proximally and distally as desired. Similarly, the male rotating homeostasis valve 1936 is rotated or otherwise manipulated in order to rotate the outer shaft 120 (and inflow capture device 122 attached thereto) or move the outer shaft 120 (and inflow capture device 122 attached thereto) proximally and distally as desired. The proximal end 1904 of the delivery system 1900 includes a guidewire inlet 1912, which is described in more detail below. The components of the proximal end 1904 of the delivery system 1900 are exemplary. Other alternative or additional components of the proximal end 1904 of the delivery system 1900 are also contemplated by the invention.

Figure 19A:
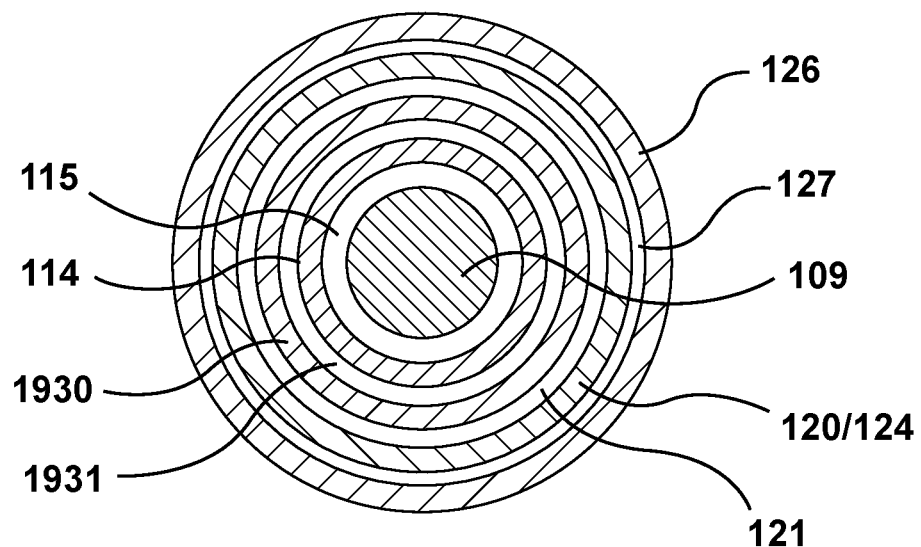
FIG. 19A is a cross-sectional view of the delivery system of FIG. 19 taken along line A-A of FIG. 9.

FIG. 19 shows the distal end 1902 of the delivery system 1900 in an assembled configuration, without a prosthetic valve device attached or loaded thereto. FIG. 19A is a cross-sectional view of the delivery system of FIG. 19 taken along line A-A of FIG. 19. As best shown on FIG. 19A, the delivery system 1900 includes at least four concentric tubular components. More particularly, the delivery system 1900 includes the inner shaft 114 which defines the guidewire lumen 115, the intermediate shaft 1930 which defines a lumen 1931 and is slidingly disposed over the inner shaft 114, the outer shaft 120 which defines the lumen 121 and is slidingly disposed over the intermediate shaft 1930, and the retractable sheath 126 which defines the lumen 127 and is slidingly disposed over the outer shaft 120 to hold the prosthetic valve device 150 in a radially collapsed or compressed configuration during delivery. The delivery system 1900 may further include the outer sleeve 116 that is disposed over the retractable sheath 126 to keep blood from leaking back around the delivery system 1900.

The inner shaft 114, as previously described with respect to the delivery system 100, includes the tapered distal tip 118 attached thereto at its distal end and is attached to the guidewire lumen inlet 1912 at its proximal end such that the inner shaft 114 may be tracked over the guidewire 109. Inner shaft 114 may be independently advanced or retracted through other components of the delivery system 1900 by moving the guidewire lumen inlet 1912 to which it is attached.

The intermediate shaft 1930 is slidingly disposed over the inner shaft 114 and is independently rotatable with respect to the other shaft components of the delivery system 1920. The intermediate shaft 1930 may be formed of one or more polymeric materials, non-exhaustive examples of which include polyethylene, polyethylene block amide copolymer (PEBA), polyamide and/or combinations thereof, either laminated, blended or co-extruded. Optionally, the intermediate shaft 1930 may be formed as a composite having a reinforcement layer incorporated within a polymeric body in order to enhance strength and/or torque-ability. Suitable reinforcement layers include braiding, wire mesh layers, embedded axial wires, embedded helical or circumferential wires, hypotubes, and the like. In this embodiment, the outflow capture device 1928 is coupled to a distal end of the intermediate shaft 1930. When the intermediate shaft 1930 is rotated via the male rotating homeostasis valve 1936 of the handle 1910, the intermediate shaft 1930 and the outflow capture device 1928 collectively rotate as an assembly.

Thus, movement of the intermediate shaft 1930, as controlled by the handle 1910, controls movement or rotation of the outflow capture device 1928. The intermediate shaft 1930 is also configured to be independently moved or translated in a longitudinal or axial direction relative to the other shaft components of the delivery system 1400. In an embodiment, the delivery system 1900 is configured to permit the intermediate shaft 1930 to move or translate between 10-65 mm.

FIG. 20 is an enlarged side perspective view of the distal end of the delivery system 1900, while FIG. 21 is an enlarged side perspective view of the outflow capture device 1928 shown removed from the delivery system 1900 for illustrative purposes only. In this embodiment, the outflow capture device 1928 includes the coil 1928A including at least one complete winding about a longitudinal axis of the intermediate shaft 1930 and is configured for engagement through openings in the plurality of second attachment members 159. In an embodiment, the coil 1928A of the outflow capture device 1928 has an overall tapered profile with a distal end thereof having a larger diameter than a proximal end thereof. The outflow capture device 1928 also includes a hub 1932 attached to a distal end of the coil 1928. The hub 1932 is configured to attach to the intermediate shaft 1930 such that the outflow capture device 1928 moves and rotates with the intermediate shaft 1930 as an assembly. In an embodiment, the hub 1932 may include a plurality of threads on an inner surface thereof and the distal end of the intermediate shaft 1930 may include mating threads on an outer surface thereof such that the hub 1932 and the intermediate shaft 1930 may have a threaded relationship. The hub 1932 is configured to abut against a proximal end of the distal tip 118 such that there is a smooth transition between the two components. The outflow capture device 1928 further includes a deflector 1933 having a tapered outer surface mounted on the intermediate shaft 1930 adjacent to a proximal end of the coil 1928A. More particularly, the outer surface of the deflector 1933 tapers in a distal to proximal direction from the proximal end of the coil 1928A to an outer surface of the intermediate shaft 1930. A distal end of the deflector 1930 includes a channel 1935 formed therein for receiving the proximal end of the coil 1928A. Due to its tapered outer surface, the deflector 1930 allows the outflow capture device 1928, and the outflow end 158 of the prosthetic valve device 150 coupled thereto, to be re-sheathed or recaptured without damage to the delivery system 1900, the prosthetic valve device 150, or the anatomy. In an embodiment, the deflector 1930 is formed from a relatively soft material such as rubber or silicone. In an embodiment, the deflector 1930 is non-movably mounted to an outer surface of the intermediate shaft 1930 adjacent to the coil 1928A as shown in FIG. 21. In another embodiment, the deflector 1930 may be movably or slidably mounted on the outer surface of the intermediate shaft 1930 such that the longitudinal or axial position thereof may be chosen by the operator in order to best protect the anatomy and/or to assist in loading the prosthetic valve device 150. For example, an operator may position the deflector 1930 at a spaced apart location from the coil 1928A during loading of the prosthetic valve device 150 and may slide the deflector 1930 in a distal direction to position the deflector 1930 adjacent to or abutting against the coil 1928A after the prosthetic valve device 150 is loaded. In another embodiment (now shown), the deflector 1930 may be non-movably mounted to an outer surface of the intermediate shaft 1930 at a spaced apart location from the coil 1928A.

The outer shaft 120, as previously described with respect to the delivery system 100, is slidingly disposed over the intermediate shaft 1930. Surrounding the outer shaft 120 is the reinforcement layer 124, which is attached or otherwise bonded to the outer shaft 120 and serves to reinforce the outer shaft 120. Movement of the outer shaft 120 is controlled by the handle 1910 at the proximal end 1904 of the delivery system 1900. The female rotating homeostasis valve 1934 of the handle 1910 is rotated or otherwise manipulated in order to rotate the outer shaft 120 or move the outer shaft 120 proximally and distally as desired. The inflow capture device 122 is coupled to a distal end of the outer shaft 120. When the outer shaft 120 is rotated via the handle 1910, the outer shaft 120 and the inflow capture device 122 collectively rotate as an assembly. Thus, movement of the outer shaft 120, as controlled by the handle 1910, controls movement or rotation of the inflow capture device 122. In this embodiment, the inflow capture device 122 is a coil including at least one complete winding about a longitudinal axis of the outer shaft 120 and is configured for engagement through openings in the plurality of first attachment members 157.

The inflow and outflow capture devices 122, 1928 provides means for releasably attaching the prosthetic valve device 150 onto the delivery system 1900 by holding the inflow and outflow ends 156, 158, respectively, of the prosthetic valve device 150 on the delivery system 1900 during delivery. The inflow capture device 122 is configured to hold the inflow end 156 of the prosthetic valve device 150 by engaging through openings in the plurality of first attachment members 157, while the outflow capture device 1928 is configured to hold the outflow end 158 of the prosthetic valve device 150 by engaging through openings in the plurality of second attachment members 159. The inflow and outflow capture devices 122, 1928 are further configured to release the prosthetic valve device 150 from the delivery system 1900 in situ. The intermediate shaft 1930 is rotatable in order to release the plurality of second attachment members 159. Stated another way, when the outflow capture device 1928 rotates or turns, the plurality of second attachment members 159 disengage or detach from the outflow capture device 1928, thus releasing the outflow end 158 of the prosthetic valve device 150. Similarly, the outer shaft 120 is rotatable in order to release the plurality of first attachment members 159. Stated another way, when the inflow capture device 122 rotates or turns, the plurality of first attachment members 157 disengage or detach from the inflow capture device 122, thus releasing the inflow end 156 of the prosthetic valve device 150. The speed that the inflow and outflow ends 156, 158 of the prosthetic valve device 150 are released from the delivery system 1900 are controlled by the rate of rotation of the inflow and outflow capture devices 122, 1928, respectively, therefore preventing uncontrolled release of the prosthetic valve device 150. The inflow and outflow ends 156, 158 of the prosthetic valve device 150 are selectively held, restrained, or otherwise controlled by the inflow and outflow capture devices 122, 1928, respectively, until the accurate positioning of the prosthetic valve device 150 is established. The coils of the inflow and outflow capture devices 122, 1928 have opposite winding directions such that the plurality of first attachment members 157 coupled to the inflow capture device 122 move in a distal direction along the coil winding(s) to release the inflow end 156 of the prosthetic valve device 150 while the plurality of second attachment members 159 coupled to the outflow capture device 1928 move in a proximal direction along the coil winding(s) to release the outflow end 158 of the prosthetic valve device 150.

The prosthetic valve device 150 is loaded onto the delivery system 1900 in the same manner as described above in FIGS. 5-9 with respect to the delivery system 100. In order to load or attach the prosthetic valve device 150 to each of the inflow and outflow capture devices 122, 1928 of the delivery system 1900, the loading rail 540 is utilized and subsequently removed. The first and second attachment members 157, 159 of the prosthetic valve device 150 may be loaded onto the respective capture device in a consecutive order or a non-consecutive order, as described above with respect to loading the prosthetic valve device 150 onto the delivery system 100. The loading funnel 560 is used to further compress the prosthetic valve device 150 for eventual enclosure in the delivery system 1400 and is subsequently removed after the prosthetic valve device 150 is retracted into the retractable sheath 126, as described above with respect to the delivery system 100 in FIGS. 8 and 9.

The prosthetic valve device 150 is deployed from the delivery system 1900 in a similar manner as described above in FIGS. 10-13 with respect to the delivery system 100. More particularly, in order to deploy or release the prosthetic valve device 150 once it has been positioned at its desired location in situ in the vasculature or in a heart valve annulus, for example, the retractable sheath 126 is either retracted proximally, or the assembly of the outer shaft 120, the intermediate shaft 1930, and the prosthetic valve device 150 is pushed out the end of the retractable sheath 126. Notably, the pushability of the assembly of the outer shaft 120, the intermediate shaft 1930, and the prosthetic valve device 150 is improved with both the inflow and outflow ends of the prosthetic valve device 150 being constrained by the inflow and outflow capture devices 122, 1428 because such constraint prevents any inadvertent buckling of the prosthetic valve device 150 that may otherwise occur when being pushed in a distal direction without both the inflow and outflow ends of the prosthetic valve device 150 being constrained by the inflow and outflow capture devices 122, 1428. The retractable sheath 126 is at least partially retracted to expose at least the outflow end 158 of the prosthetic valve device 150 and the prosthetic valve device 150 is partially expanded, with the outflow end 158 of the prosthetic valve device 150 still engaged or attached to the outflow capture device 1928 of the delivery system 1400. At this stage of deployment, positioning of the delivery system 1400 may still be adjusted and/or the retractable sheath 126 may be distally advanced to recapture the prosthetic valve device 150. The intermediate shaft 1930 having the outflow capture device 1928 attached thereto, and the outer shaft 120 having the inflow capture device 122 attached thereto, may be independently moved or translated in a longitudinal or axial direction in order to assist in deployment and/or positioning of the prosthetic valve device 150. More particularly, even if the retractable sheath 126 is retracted to expose the entire length of the prosthetic valve device 150, the prosthetic valve device 150 may essentially be stretched or tensioned via translation of the proximal and/or outflow capture devices 122, 1928. Since the prosthetic valve device 150 may be stretched or tensioned, the profile thereof may be sufficiently reduced to enable to the retractable sheath 126 to be distally advanced to recapture the prosthetic valve device 150 and thus allow repositioning thereof in situ.

The outflow end 158 of the prosthetic valve device 150 is then released from the outflow capture device 1928 and permitted to self-expand. More particularly, the outflow capture device 1928 is rotated until the plurality of second attachment members 159 are all released from the windings of the outflow capture device 1928. In this embodiment, the outflow capture device 1928 is rotated via rotation of the intermediate shaft 130, which is independently rotated relative to the other shaft components of the delivery system 1900 via handle 1910.

The retractable sheath 126 is then fully retracted to expose an entire length of the prosthetic valve device 150, with the inflow end 156 of the prosthetic valve device 150 still engaged or attached to the inflow capture device 122 of the delivery system 1900. However, the retractable sheath 126 may have been fully retracted to expose an entire length of the prosthetic valve device 150 prior to releasing the outflow end 158 of the prosthetic valve device 150 from the outflow capture device 128.

The inflow end 156 of the prosthetic valve device 150 is then released from the inflow capture device 122 and permitted to self-expand. More particularly, in order to fully release the prosthetic valve device 150 from the delivery system 1900, the inflow capture device 122 is rotated until the plurality of first attachment members 157 are all released from the windings of the inflow capture device 122. As described above, the inflow capture device 122 is rotated via rotation of the outer shaft 120, which is independently rotated relative to the other components of the delivery system 1900 via the handle 1910. Advantageously, blood can flow through the delivery system 1900 at this point, thereby maintaining relatively normal heart function during the procedure. Once the prosthetic valve device 150 is released from the delivery system 1900, the delivery system 1900 may be removed from the patient.

In an embodiment, after the prosthetic valve device 150 is released from the delivery system 1900, the user may move the intermediate shaft 1930 and the outer shaft 120 relative to each other in order lock or join the coils of the proximal and outflow capture devices 122, 1928 together prior to removing the delivery system 1900 from the patient. Locking or joining the coils of the proximal and outflow capture devices 122, 1928 together prior to removing the delivery system 1900 from the patient may reduce inadvertent damage to the anatomy during removal.

Figure 22:
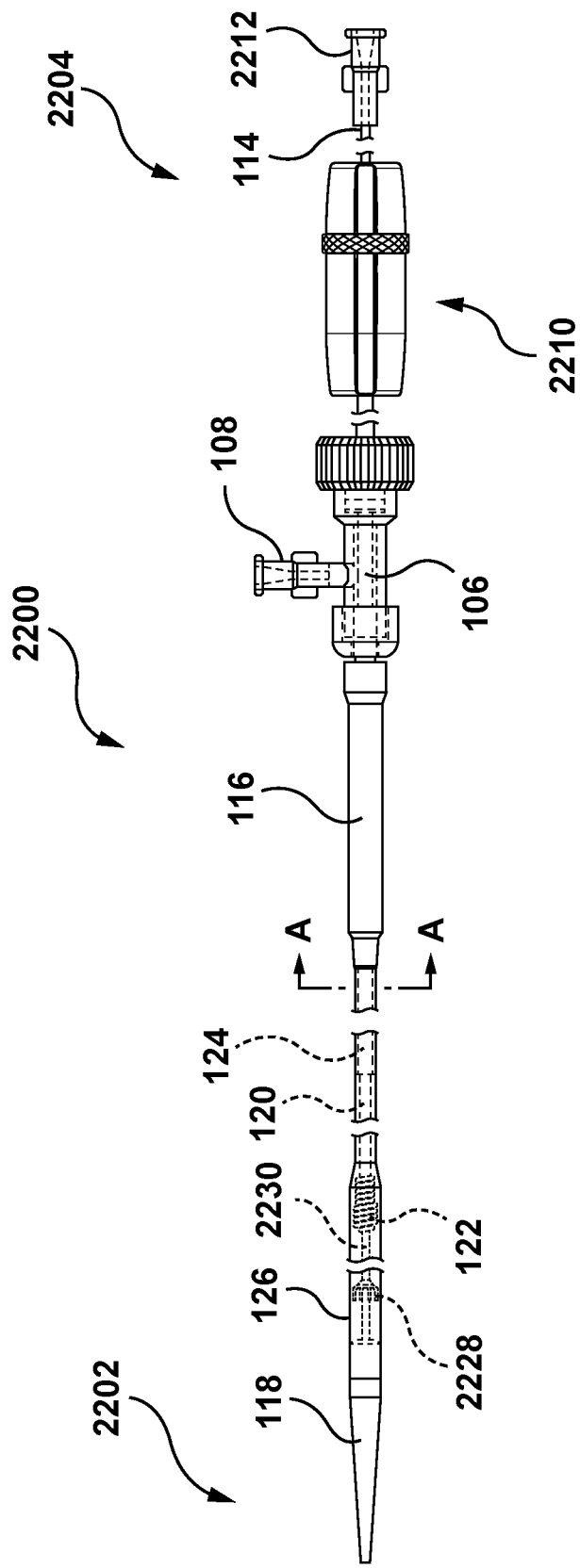
FIG. 22 is a side view of a delivery system according to an embodiment hereof, wherein the delivery system includes an inflow capture device configured to engage an inflow end of a prosthetic valve device and an outflow capture device configured to engage an outflow end of the prosthetic valve device when the prosthetic valve device is loaded within the delivery system.

FIG. 22 is a side view of a delivery system 2200 according to another embodiment hereof. The delivery system 2200 is configured to receive the prosthetic valve device 150 and percutaneously deliver the prosthetic valve device 150 in a compressed configuration to a treatment site in situ. More particularly, similar to the delivery system 100, the delivery system 2200 includes the inflow capture device 114 configured to engage or attach to the plurality of first attachment members 157 on or near the inflow end 156 of the prosthetic valve device 150 and an outflow capture device 2228 configured to engage or attach to the plurality of second attachment members 159 on or near the outflow end 158 of the prosthetic valve device 150. In the embodiment of FIGS. 22-25, the outflow capture device 2228 includes a plurality of distally extending fingers 2228A configured for engagement through openings in the plurality of second attachment members 159 that is retractable to release the plurality of second attachment members 159 and the inflow capture device 114 is a coil configured for engagement through openings in the plurality of first attachment members 157 that is rotatable to release the plurality of first attachment members 157. The outflow capture device 2228 is disposed on an intermediate shaft 2230 that is disposed between the inner shaft 114 and the outer shaft 120. Intermediate shaft 2230, and the outflow capture device 2228 attached thereto, are retractable relative to the other shaft components of the delivery system 2200 to release the plurality of second attachment members 159 from the outflow capture device 2228.

The delivery system 2200 includes a distal end generally designated by the reference numeral 2202 and a proximal end generally designated by the reference number 2204. The proximal end 2204 of the delivery system 2200 remains outside of the patient, and the distal end 2202 is inserted into the patient and is delivered intravascularly to an area at or near a pulmonary valve inside the body. Other uses for the delivery system 2200 in other areas of the body, however, are also contemplated. The proximal end 2204 includes means for remotely controlling the distal end 2202 of the delivery system 2200, in particular relating to deploying or releasing the prosthetic valve device 150 from the delivery system 2200 in situ.

The components of the proximal end 2204 of the delivery system 2200 may include those shown in FIG. 22, although additional and/or alternative components are also contemplated. FIG. 22 includes the first rotating homeostasis valve 106 previously described with respect to the delivery system 100, the side access port 108 previously described with respect to the delivery system 100, and a handle 2210 previously described with respect to the delivery system 100. The handle 2210 controls the components of the distal end 2204 as described in more detail below by independent manipulation of two portions of the handle 2210. The proximal end 2204 of the delivery system 2200 includes a guidewire inlet 2212, which is described in more detail below. The components of the proximal end 2204 of the delivery system 2200 are exemplary. Other alternative or additional components of the proximal end 2204 of the delivery system 2200 are also contemplated by the invention.

Figure 22A:
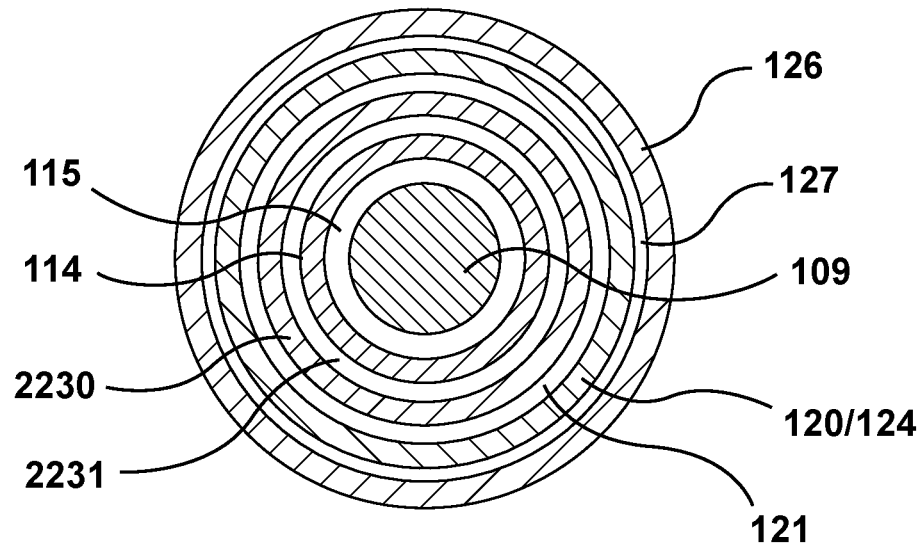
FIG. 22A is a cross-sectional view of the delivery system of FIG. 22 taken along line A-A of FIG. 22.

FIG. 22 shows the distal end 2202 of the delivery system 2200 in an assembled configuration, without a prosthetic valve device attached or loaded thereto. FIG. 22A is a cross-sectional view of the delivery system of FIG. 22 taken along line A-A of FIG. 22. As best shown on FIG. 22A, the delivery system 2200 includes at least four concentric tubular components. More particularly, the delivery system 2200 includes the inner shaft 114 which defines the guidewire lumen 115, the intermediate shaft 2230 which defines a lumen 2231 and is slidingly disposed over the inner shaft 114, the outer shaft 120 which defines the lumen 121 and is slidingly disposed over the intermediate shaft 2230, and the retractable sheath 126 which defines the lumen 127 and is slidingly disposed over the outer shaft 120 to hold the prosthetic valve device 150 in a radially collapsed or compressed configuration during delivery. The delivery system 2200 may further include the outer sleeve 116 that is disposed over the retractable sheath 126 to keep blood from leaking back around the delivery system 2200.

The inner shaft 114, as previously described with respect to the delivery system 100, includes the tapered distal tip 118 attached thereto at its distal end and is attached to the guidewire lumen inlet 2212 at its proximal end such that the inner shaft 114 may be tracked over the guidewire 109. Inner shaft 114 may be independently advanced or retracted through other components of the delivery system 2200 by moving the guidewire lumen inlet 2212 to which it is attached.

The intermediate shaft 2230 is slidingly disposed over the inner shaft 114 and is independently retractable with respect to the other shaft components of the delivery system 2220. In this embodiment, the outflow capture device 2228 is coupled to a distal end of the intermediate shaft 2230. When the intermediate shaft 2230 is retracted via the handle 2210 as will be described in more detail below, the intermediate shaft 2230 and the outflow capture device 2228 collectively retract as an assembly. Thus, longitudinal movement of the intermediate shaft 2230, as controlled by the handle 2210, controls longitudinal movement of the outflow capture device 2228. In an embodiment, the delivery system 2200 is configured to permit the intermediate shaft 2230 to move or translate between 10-30 mm.

Figure 1C:
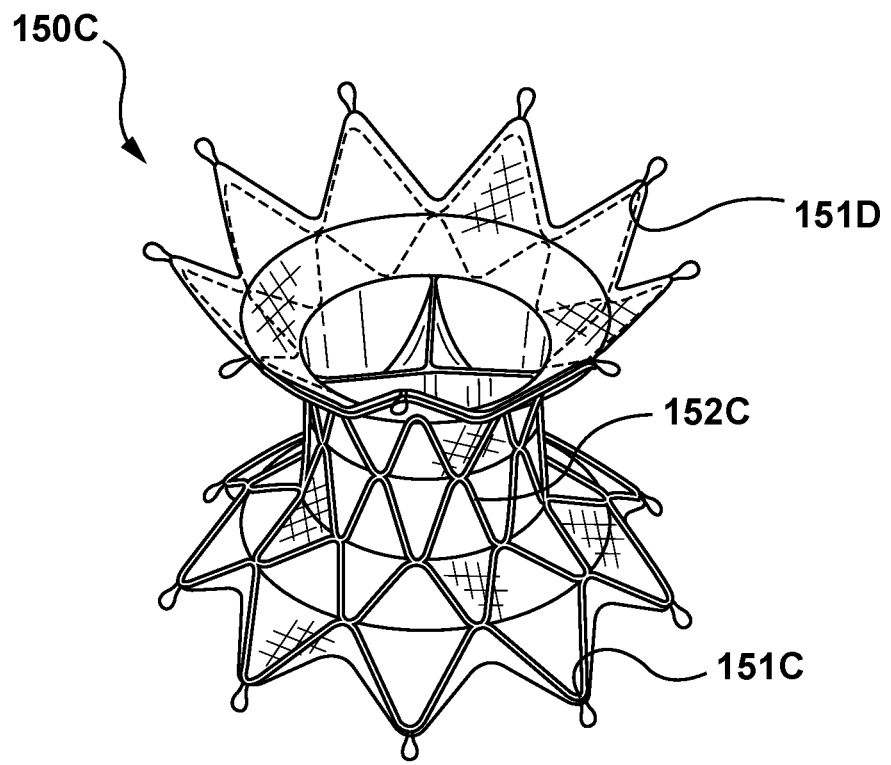
FIG. 1C is a perspective view of another exemplary prosthetic valve device that may be utilized in embodiments hereof.
Figure 23:
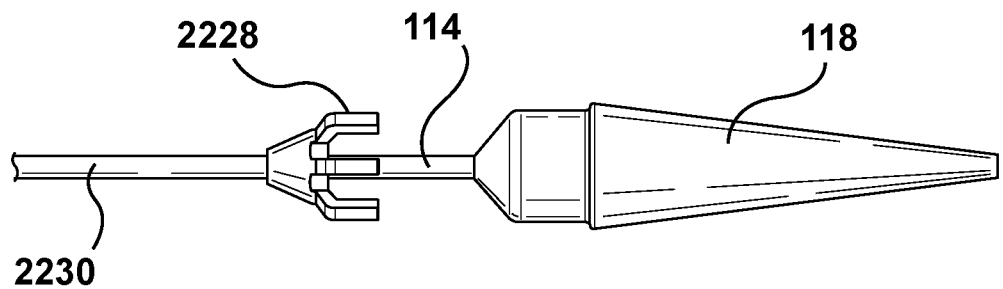
FIG. 23 is an enlarged side perspective view of a distal tip of the delivery system of FIG. 22.
Figure 24:
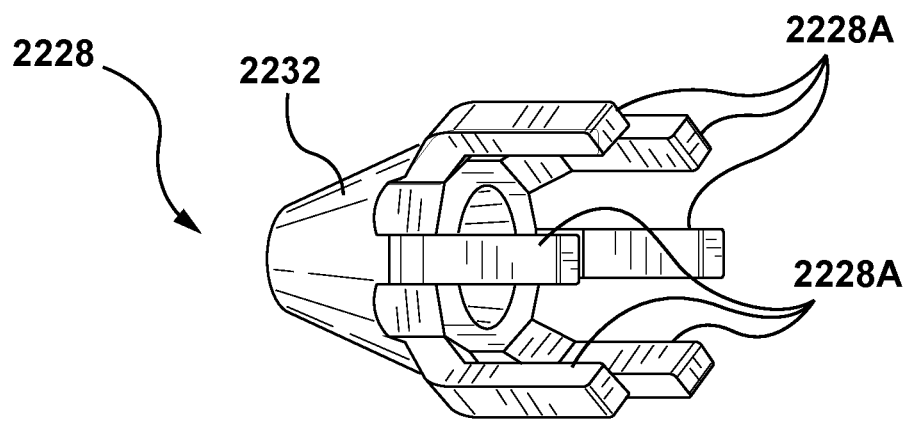
FIG. 24 is an enlarged side perspective view of the outflow capture device of the delivery system of FIG. 22, wherein the outflow capture device is shown removed from the delivery system for illustrative purposes only.

FIG. 23 is an enlarged side perspective view of the distal end of the delivery system 2200, while FIG. 24 is an enlarged side perspective view of the outflow capture device 2228 shown removed from the delivery system 2200 for illustrative purposes only. In this embodiment, the outflow capture device 2228 includes a hub 2232 and a plurality of distally extending fingers or prongs 2228A that distally extend from the hub 2232. The hub 2232 is configured to attach to the intermediate shaft 2230 such that the outflow capture device 2228 moves with the intermediate shaft 2230 as an assembly. As such, the outflow capture device 2228 is mounted on the intermediate shaft 2230 to be retractable therewith. The plurality of distally extending fingers 2228A are configured for engagement through openings in the plurality of second attachment members 159 on the prosthetic valve device 150. When the intermediate shaft 2230 is retracted, the plurality of distally extending fingers 2228A are also retracted and disengage from the plurality of second attachment members 159, thereby allowing the outflow end 158 of the prosthetic valve device 150 to self-expand. In an embodiment, the number of distally extending fingers 2228A is the same as the number of second attachment members 159 on the prosthetic valve device 150. Thus, in FIGS. 23 and 24, the outflow capture device 2228 is shown with a total of six distally extending fingers 2228A to correspond with the six second attachment members 159 of the prosthetic valve device 150. Alternatively, if the outflow capture device 2228 is configured to be utilized with the prosthetic valve device 150C of FIG. 1C, the outflow capture device 2228 may include a total of nine distally extending fingers 2228A to correspond with the nine endmost outflow crowns 151D of the prosthetic valve device 150C.

Although described above that a distally extending finger is attached (via an attachment loop) to each endmost crown of the outflow end of the prosthetic valve device 150, it will be understood by one of ordinary skill in the art that not all endmost crowns are required to be attached to a delivery system during delivery and thus not all endmost crowns are required to be attached to a distally extending finger. Further, in an embodiment, more than one attachment loop of the prosthetic valve device may be attached to a single distally extending finger such that the total number of distally extending fingers is less than the total number of attachment loops. Thus, the number of distally extending fingers is not required to equal to the number of attachment loops and/or the number of endmost crowns of the outflow end of the prosthetic valve device.

The outer shaft 120, as previously described with respect to the delivery system 100, is slidingly disposed over the intermediate shaft 2230. Surrounding the outer shaft 120 is the reinforcement layer 124, which is attached or otherwise bonded to the outer shaft 120 and serves to reinforce the outer shaft 120. Movement of the outer shaft 120 is controlled by the handle 2210 at the proximal end 2204 of the delivery system 2200. A portion of the handle 2210 is rotated or otherwise manipulated in order to rotate the outer shaft 120 or move the outer shaft 120 proximally and distally as desired. The inflow capture device 122 is coupled to a distal end of the outer shaft 120. When the outer shaft 120 is rotated via the handle 2210, the outer shaft 120 and the inflow capture device 122 collectively rotate as an assembly. Thus, movement of the outer shaft 120, as controlled by the handle 2210, controls movement or rotation of the inflow capture device 122. In this embodiment, the inflow capture device 122 is a coil including at least one complete winding about a longitudinal axis of the outer shaft 120 and is configured for engagement through openings in the plurality of first attachment members 157.

The inflow and outflow capture devices 122, 2228 provides means for releasably attaching the prosthetic valve device 150 onto the delivery system 2200 by holding the inflow and outflow ends 156, 158, respectively, of the prosthetic valve device 150 on the delivery system 2200 during delivery. The inflow capture device 114 is configured to hold the inflow end 156 of the prosthetic valve device 150 by engaging through openings in the plurality of first attachment members 157, while the outflow capture device 2228 is configured to hold the outflow end 158 of the prosthetic valve device 150 by engaging through openings in the plurality of second attachment members 159. The inflow and outflow capture devices 122, 2228 are further configured to release the prosthetic valve device 150 from the delivery system 2200 in situ. The intermediate shaft 2230 is retractable in order to release the plurality of second attachment members 159. Stated another way, when the outflow capture device 2228 retracts or is pulled in a proximal direction, the outflow capture device 2228 disengage or detach from the plurality of second attachment members 159, thus releasing the outflow end 158 of the prosthetic valve device 150. The outer shaft 120 is rotatable in order to release the plurality of first attachment members 159. Stated another way, when the inflow capture device 114 rotates or turns, the plurality of first attachment members 157 disengage or detach from the inflow capture device 122, thus releasing the inflow end 156 of the prosthetic valve device 150. The speed that the inflow and outflow ends 156, 158 of the prosthetic valve device 150 are released from the delivery system 2200 are controlled by the rate of movement of the inflow and outflow capture devices 122, 2228, respectively, therefore preventing uncontrolled release of the prosthetic valve device 150. The inflow and outflow ends 156, 158 of the prosthetic valve device 150 are selectively held, restrained, or otherwise controlled by the inflow and outflow capture devices 122, 2228, respectively, until the accurate positioning of the prosthetic valve device 150 is established.

Figure 25:
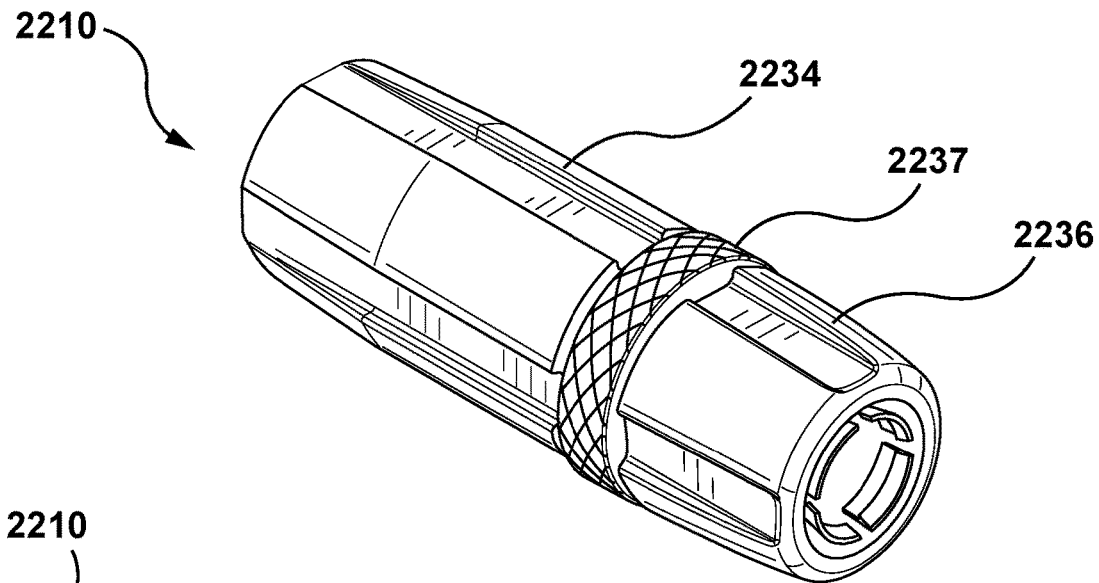
FIG. 25 is an enlarged perspective view of a handle of the delivery system of FIG. 22.
Figure 26:
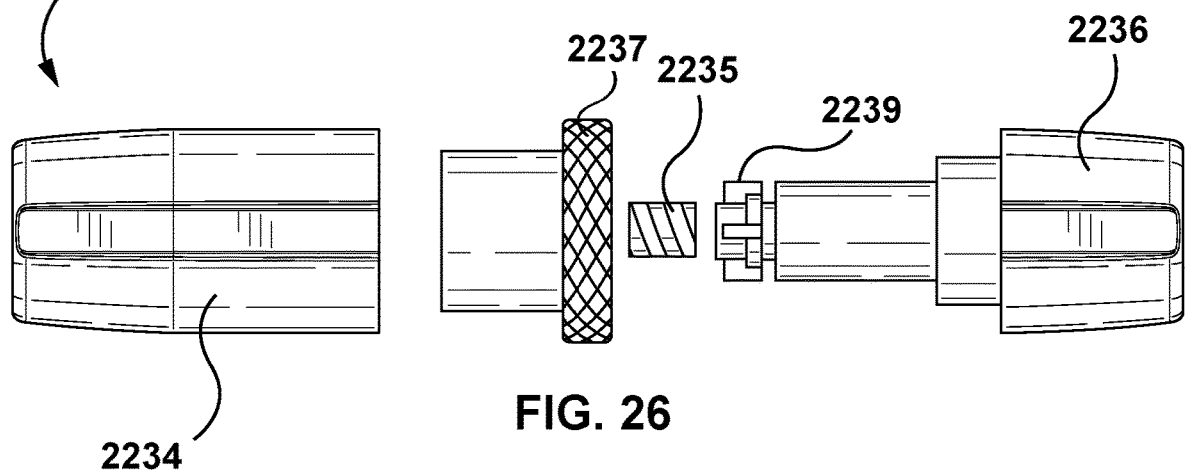
FIG. 26 is an exploded side view of the handle of FIG. 25.

The handle 2210 is shown in a perspective view and a side exploded view in FIGS. 25 and 26, respectively. The handle 2210 includes a female homeostasis valve 2234, a male homeostasis valve 2236, and a wheel actuator 2237 disposed between the homeostasis valves 2234, 2236. The female homeostasis valve 2234 is coupled to a proximal end of the outer shaft 120 such that when the female homeostasis valve 2234 is rotated by a user, the outer shaft 120 as well as the inflow capture device 122 attached thereto rotates as well. Thus, the female homeostasis valve 2234 is rotated in order to rotate the outer shaft 120 as desired. The female homeostasis valve 2234 grips or forms a fluid seal around the outer shaft 120 to prevent blood or other fluid from leaking back through the delivery system 2200. In addition, the female homeostasis valve 2234 is configured to allow wires, devices and fluid to pass through.

Figure 27:
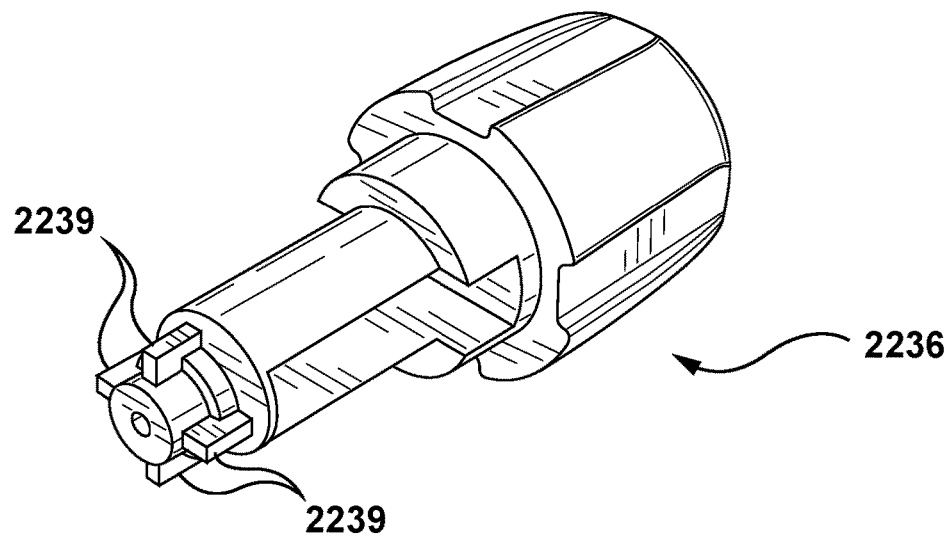
FIG. 27 is a perspective view of a male homeostasis valve of the handle of FIG. 25.

The wheel actuator 2237 is configured to cause the male homeostasis valve 2236 to move in a longitudinal or axial direction when the wheel actuator is rotated or turned by a user. As shown on FIG. 26 as well as FIG. 27, which is a perspective view of the male homeostasis valve 2236 removed from the handle 2210 for illustrative purposes only, the male homeostasis valve 2236 includes a plurality of pegs 2239 thereon for preventing rotation of the male homeostasis valve 2236 relative to the female homeostasis valve 2234. However, the male rotating homeostasis valve 2236 may longitudinally translate or slide relative to the female homeostasis valve 2234. Since the male homeostasis valve 2236 is prevented from rotating due to the pegs 2239, a threaded relationship causes the male homeostasis valve 2236 to move in a longitudinal or axial direction when the wheel actuator 2237 is rotated by an operator. More particularly, the male homeostasis valve 2236 is coupled to a proximal end of the intermediate shaft 2230 such that when the male rotating homeostasis valve 2236 moves in a longitudinal or axial direction, the intermediate shaft 2230 as well as the outflow capture device 2228 attached thereto may be moved or translated in a longitudinal or axial direction relative to the remaining components of the delivery system 2200. A boss 2235 is attached to the intermediate shaft 2230 and includes a helical threaded profile on its outer surface that interacts with the inner surface of the wheel actuator 2237. When the wheel actuator 2237 is rotated, the assembly of the boss 2235, the intermediate shaft 2230, and the male homeostasis valve 2236 is prevented from rotating due to the pegs 2239 on the male homeostasis valve 2236. As a result, when the wheel actuator 2237 is rotated, the boss 2235 and the intermediate shaft 2230 attached thereto are moved proximally and distally as desired. The male homeostasis valve 2236 grips or forms a fluid seal around the intermediate shaft 2230 to prevent blood or other fluid from leaking back through the delivery system 2200.

Figure 28:
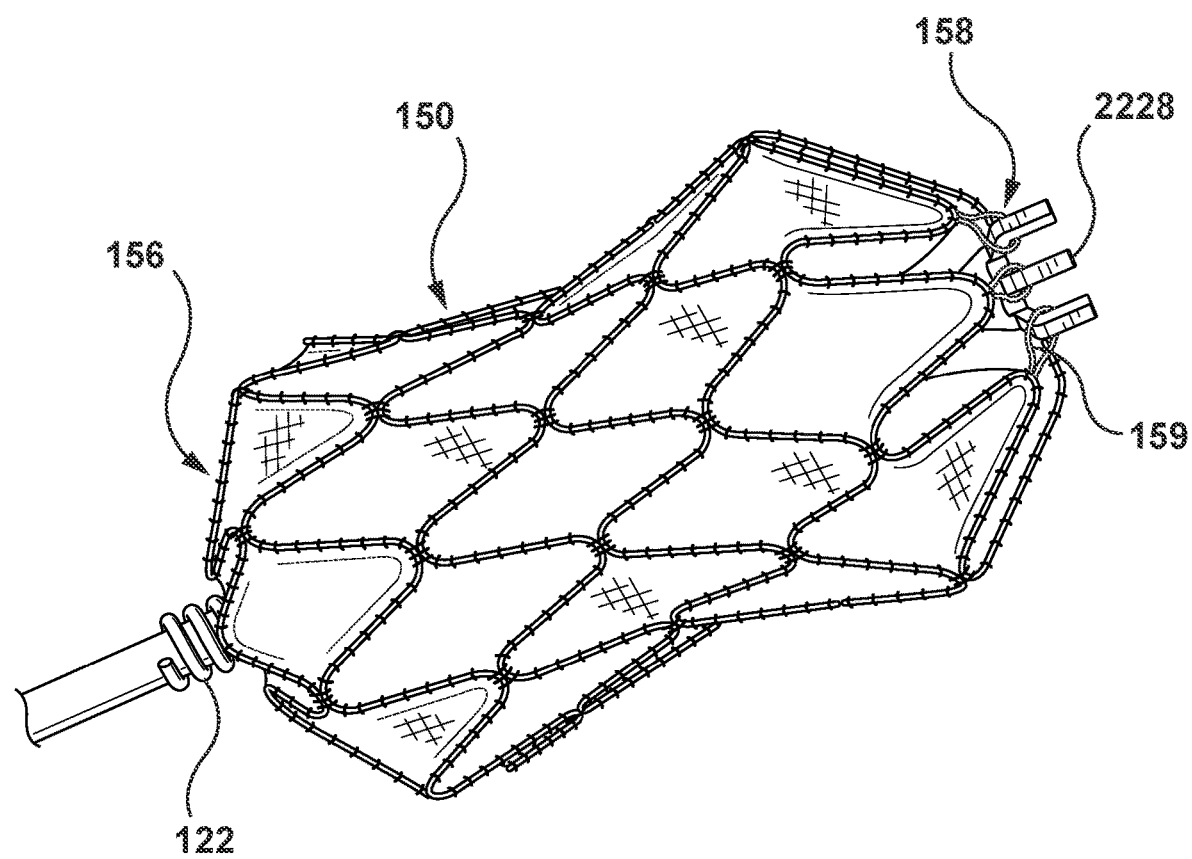
FIG. 28 is a side perspective view of a distal end of the delivery system of FIG. 22 and the prosthetic valve device of FIG. 1 with the inflow capture device of the delivery system engaged or attached to the inflow end of the prosthetic valve device and the outflow capture device of the delivery system engaged or attached to the outflow end of the prosthetic valve device.

The prosthetic valve device 150 is loaded onto the delivery system 2200 in a similar manner as described above in FIGS. 5-9 with respect to the delivery system 100. In order to load or attach the prosthetic valve device 150 to the inflow capture device 114 of the delivery system 2200, the loading rail 540 is utilized and subsequently removed. The first attachment members 157 of the prosthetic valve device 150 may be loaded onto the inflow capture device 114 in a consecutive order or a non-consecutive order, as described above with respect to loading the prosthetic valve device 150 onto the delivery system 100. FIG. 28 is a side perspective view of the distal end 2202 of the delivery system 2200 with the prosthetic valve device 150 loaded thereon, with the inflow and outflow ends 156, 158, of the prosthetic valve device 150 engaged or attached to the inflow and outflow capture devices, 122, 2228, of the delivery system 2200. In order to load or attach the second attachment members 159 of the prosthetic valve device 150 to the outflow capture device 2228 of the delivery system 2200, the plurality of second attachment members 159 are hooked onto or otherwise disposed around the plurality of distally extending fingers 2228A of the outflow capture device 2228 as shown in FIG. 28. The loading funnel 560 would then be used to further compress the prosthetic valve device 150 for eventual enclosure in the delivery system 2200 and is subsequently removed after the prosthetic valve device 150 is retracted into the retractable sheath 126, as described above with respect to the delivery system 100 in FIGS. 8 and 9.

The prosthetic valve device 150 is deployed from the delivery system 2200 in a similar manner as described above in FIGS. 10-13 with respect to the delivery system 100. More particularly, in order to deploy or release the prosthetic valve device 150 once it has been positioned at its desired location in situ in the vasculature or in a heart valve annulus, for example, the retractable sheath 126 is either retracted proximally, or the assembly of the outer shaft 120, the intermediate shaft 2230, and the prosthetic valve device 150 is pushed out the end of the retractable sheath 126. Notably, the pushability of the assembly of the outer shaft 120, the intermediate shaft 2230, and the prosthetic valve device 150 is improved with both the inflow and outflow ends of the prosthetic valve device 150 being constrained by the inflow and outflow capture devices 122, 2228 because such constraint prevents any inadvertent buckling of the prosthetic valve device 150 that may otherwise occur when being pushed in a distal direction without both the inflow and outflow ends of the prosthetic valve device 150 being constrained by the inflow and outflow capture devices 122, 2228. The retractable sheath 126 is at least partially retracted to expose at least the outflow end 158 of the prosthetic valve device 150 and the prosthetic valve device 150 is partially expanded, with the outflow end 158 of the prosthetic valve device 150 still engaged or attached to the outflow capture device 2228 of the delivery system 2200. At this stage of deployment, positioning of the delivery system 2200 may still be adjusted and/or the retractable sheath 126 may be distally advanced to recapture the prosthetic valve device 150. The intermediate shaft 2230 having the outflow capture device 2228 attached thereto, and the outer shaft 120 having the inflow capture device 122 attached thereto, may be independently moved or translated in a longitudinal or axial direction in order to assist in deployment and/or positioning of the prosthetic valve device 150. More particularly, even if the retractable sheath 126 is retracted to expose the entire length of the prosthetic valve device 150, the prosthetic valve device 150 may essentially be stretched or tensioned via translation of the proximal and/or outflow capture devices 122, 2228. Since the prosthetic valve device 150 may be stretched or tensioned, the profile thereof may be sufficiently reduced to enable to the retractable sheath 126 to be distally advanced to recapture the prosthetic valve device 150 and thus allow repositioning thereof in situ.

The outflow end 158 of the prosthetic valve device 150 is then released from the outflow capture device 2228 and permitted to self-expand. More particularly, the outflow capture device 2228 is retracted until the plurality of second attachment members 159 are all released from the outflow capture device 2228. In this embodiment, the outflow capture device 2228 is retracted via retraction of the intermediate shaft 2230, which is independently retracted relative to the other components of the delivery system 2200 via handle 2210. The intermediate shaft 2230 having the outflow capture device 2228 attached thereto, and the outer shaft 120 having the inflow capture device 122 attached thereto, may be independently moved or translated in a longitudinal or axial direction in order to assist in deployment and/or positioning of the prosthetic valve device 150.

The retractable sheath 126 is then fully retracted to expose an entire length of the prosthetic valve device 150, with the inflow end 156 of the prosthetic valve device 150 still engaged or attached to the inflow capture device 122 of the delivery system 2200. However, the retractable sheath 126 may have been fully retracted to expose an entire length of the prosthetic valve device 150 prior to releasing the outflow end 158 of the prosthetic valve device 150 from the outflow capture device 128.

The inflow end 156 of the prosthetic valve device 150 is then released from the inflow capture device 114 and permitted to self-expand. More particularly, in order to fully release the prosthetic valve device 150 from the delivery system 2200, the inflow capture device 114 is rotated until the plurality of first attachment members 157 are all released from the windings of the inflow capture device 114. As described above, the inflow capture device 114 is rotated via rotation of the outer shaft 120, which is independently rotated relative to the other components of the delivery system 2200 via the handle 2210. Advantageously, blood can flow through the delivery system 2200 at this point, thereby maintaining relatively normal heart function during the procedure. Once the prosthetic valve device 150 is released from the delivery system 2200, the delivery system 2200 may be removed from the patient.

As further described in U.S. Pat. No. 9,364,324 to Rafiee, herein incorporated by reference in its entirety, any embodiment described herein may include dye injection ports (not shown) near the distal end of the delivery system, and at or near the proximal end of the retractable sheath 126. The dye injection ports include a plurality of apertures through the retractable sheath 126 and to the interior of the delivery system such that dye introduced at the proximal end of the delivery system travels through the delivery system and out through the dye injection ports. The purpose of the dye injection is to allow for proximal visual alignment of the prosthetic valve device 150 being delivered. In particular, during delivery of the prosthetic valve device 150, a partially deployed prosthetic valve device 150 blocks flow. The dye injection ports will introduce dye into the right ventricular chamber and allow for precise alignment of the prosthetic valve device 150 in the right ventricular outflow tract. In an embodiment, dye injection is used together with fluoroscopy for visualization. However, visualization may be achieved by using a procedure chosen from the group consisting of fluoroscopy, echocardiography, intravascular ultrasound, angioscopy and real-time magnetic resonance imaging, for examples. However, other similar methods of visualizing the area are also contemplated for use with the dye injection. Additionally, any embodiment described herein may include purging vents located on the tapered distal tip 118 of the delivery system. The purpose of the purging vents is to allow fluids, such as saline, that is injected into the delivery system (such as by an access port like that of 108 in delivery systems described herein) is able to escape the delivery system. Such fluid may escape through a plurality of purging ports located near the distal end of the delivery system, rather than increase the pressure inside of the delivery system.

In the case of a the prosthetic valve device made using bovine jugular vein or other preserved biological tissue, such as pericardial tissue, the valve can be sterilized, stored and shipped separately in a buffered glutaraldehyde solution, and may or may not be pre-mounted on the delivery system. When utilized during loading, a loading rail may be pre-mounted or pre-loaded onto each of the inflow and outflow ends of the prosthetic valve device 150 as stored. However, it is possible that the prosthetic valve device 150 can also be pre-mounted on the delivery system if the system with the prosthetic valve device 150 mounted thereon is similarly sterilized and kept in a sterile environment. In many cases, however, an implanting physician or an assistant will perform the step of mounting the prosthetic valve device 150 to the delivery system, as described above.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A delivery system for delivery of a prosthetic device to a body lumen, the prosthetic device comprising an inflow end and an outflow end, a central lumen therethrough, a plurality of first attachment members located at or near the inflow end, and a plurality of second attachment members located at or near the outflow end, the delivery system comprising:
    an inner shaft having a distal tip, wherein the inner shaft includes a coil proximal to the distal tip, the coil of the inner shaft configured for engagement through openings in the plurality of second attachment members on the prosthetic device, wherein the coil of the inner shaft includes at least a first complete winding configured about a longitudinal axis of the inner shaft, and wherein the coil of the inner shaft includes a polymeric sleeve disposed over an outer surface thereof, the polymeric sleeve being attached to and proximally extending from the distal tip of the inner shaft, wherein the polymeric sleeve is formed from a material that is sufficiently soft and flexible to be rolled or flipped;
    an outer shaft slidingly disposed over the inner shaft, wherein the outer shaft includes a coil on a distal end thereof, the coil of the outer shaft configured for engagement through openings in the plurality of first attachment members on the prosthetic device, wherein the coil of the outer shaft includes at least a first complete winding configured about a longitudinal axis of the outer shaft; and
    a retractable sheath slidingly disposed over the outer shaft to hold the prosthetic device in a radially compressed configuration for delivery to a body lumen,
    wherein the inner shaft is rotatable relative to the outer shaft in order to control release the plurality of second attachment members and the outer shaft is rotatable relative to the retractable sheath and the inner shaft in order to control the release of the plurality of first attachment members, such that the release of the plurality of second attachment members is configured to be controlled separately from the release of the plurality of first attachment members by different components of the delivery system.

2. The delivery system of claim 1, further comprising the prosthetic device, wherein the coil of the outer shaft includes at least the first complete winding configured about the longitudinal axis of the outer shaft and a second complete winding configured about the longitudinal axis of the outer shaft, and wherein when the prosthetic device is in the radially compressed configuration, each attachment member of the plurality of first attachment members is attached to the coil of the outer shaft and the plurality of first attachment members are attached to the first and second complete windings of the coil of the outer shaft in a non-consecutive manner.

3. The delivery system of claim 2, wherein the plurality of first attachment members include at least a first set of first attachment members and a second set of first attachment members, and wherein each attachment member of the first set of first attachment members is disposed adjacent to at least one attachment member of the second set of first attachment members, and wherein when the prosthetic device is in the radially compressed configuration, the first complete winding of the coil of the outer shaft engages through openings in the first set of first attachment members and the second complete winding of the coil of the outer shaft engages through openings in the second set of first attachment members.

4. The delivery system of claim 2, wherein the plurality of first attachment members include at least a first set of first attachment members and a second set of first attachment members, and wherein each attachment member of the first set of first attachment members is disposed between two attachment members of the second set of first attachment members, and wherein when the prosthetic device is in the radially compressed configuration, the first complete winding of the coil of the outer shaft engages through openings in the first set of first attachment members and the second complete winding of the coil of the outer shaft engages through openings in the second set of first attachment members.

5. The delivery system of claim 2, wherein the coil of the inner shaft includes at least the first complete winding configured about the longitudinal axis of the inner shaft and a second complete winding configured about the longitudinal axis of the inner shaft, and wherein when the prosthetic device is in the radially compressed configuration, each attachment member of the plurality of second attachment members is attached to the coil of the inner shaft and the plurality of second attachment members are attached to the first and second complete windings of the coil of the inner shaft in a non-consecutive manner.

6. The delivery system of claim 5, wherein the plurality of second attachment members include at least a first set of second attachment members and a second set of second attachment members, and wherein each attachment member of the first set of second attachment members is disposed adjacent to at least one attachment member of the second set of second attachment members, and wherein when the prosthetic device is in the radially compressed configuration, the first complete winding of the coil of the inner shaft engages through openings in the first set of second attachment members and the second complete winding of the coil of the inner shaft engages through openings in the second set of second attachment members.

7. The delivery system of claim 5, wherein the plurality of second attachment members include at least a first set of second attachment members and a second set of second attachment members, and wherein each attachment member of the first set of second attachment members is disposed between two attachment members of the second set of second attachment members, and wherein when the prosthetic device is in the radially compressed configuration, the first complete winding of the coil of the inner shaft engages through openings in the first set of the second attachment members and the second complete winding of the coil of the inner shaft engages through openings in the second set of second attachment members.

8. The delivery system of claim 1, wherein the plurality of first attachment members include loops and the plurality of second attachment members include loops.

9. A delivery system for delivery of a prosthetic device to a body lumen, the prosthetic device comprising an inflow end and an outflow end, a central lumen therethrough, a plurality of first attachment members located at or near the inflow end, and a plurality of second attachment members located at or near the outflow end, the system comprising:

a first shaft including a distal tip attached thereto and an outflow capture device mounted on a distal end thereof, the outflow capture device configured for engagement through openings in the plurality of second attachment members on the prosthetic device, wherein the outflow capture device includes a polymeric sleeve disposed over an outer surface thereof, the polymeric sleeve being attached to and proximally extending from the distal tip of the first shaft, wherein the polymeric sleeve is formed from a material that is sufficiently soft and flexible to be rolled or flipped;

a second shaft slidingly disposed over the first shaft, wherein the second shaft includes an inflow capture device mounted on a distal end thereof, the inflow capture device configured for engagement through openings in the plurality of first attachment members on the prosthetic device; and a retractable sheath slidingly disposed over the second shaft to hold the prosthetic device in a radially compressed configuration for delivery to a body lumen, wherein the first shaft is moveable relative to the second shaft in order to control release the plurality of second attachment members and the second shaft is moveable relative to the retractable sheath and the first shaft in order to selectively control the release of the plurality of first attachment members such that the release of the plurality of second attachment members is configured to be controlled separately from the release of the plurality of first attachment members by different components of the delivery system.

10. The delivery system of claim 9, wherein the first shaft is rotatable relative to the second shaft in order to release the plurality of second attachment members.

11. The delivery system of claim 10, wherein the outflow capture device is a coil that includes at least a first complete winding configured about a longitudinal axis of the first shaft and the coil of the first shaft being mounted on the first shaft to be rotatable therewith, and the inflow capture device is a coil that includes at least a first complete winding configured about a longitudinal axis of the second shaft and the coil of the second shaft being mounted on the second shaft to be rotatable therewith.

12. The delivery system of claim 9, further comprising a third shaft including a distal tip attached thereto, wherein the first shaft is slidingly disposed over the third shaft.

13. The delivery system of claim 12, wherein the first shaft is retractable relative to the third shaft and to the second shaft in order to release the plurality of second attachment members.

14. The delivery system of claim 13, wherein the outflow capture device includes a plurality of distally extending fingers, the plurality of distally extending fingers configured for engagement through openings in the plurality of second attachment members on the prosthetic device and the plurality of distally extending fingers being mounted on the first shaft to be retractable therewith.

15. The delivery system of claim 12, wherein the first shaft is rotatable relative to the third shaft and to the second shaft in order to release the plurality of second attachment members.

16. The delivery system of claim 15, wherein the outflow capture device is a coil that includes at least a first complete winding configured about a longitudinal axis of the first shaft and the coil of the first shaft being mounted on the first shaft to be rotatable therewith, and the inflow capture device is a coil that includes at least a first complete winding configured about a longitudinal axis of the second shaft and the coil of the second shaft being mounted on the second shaft to be rotatable therewith.

17. The delivery system of claim 9, wherein the plurality of first attachment members include loops and the plurality of second attachment members include loops.

18. A system comprising:

a prosthetic device including an inflow end having a plurality of endmost inflow crowns and an outflow end having a plurality of endmost outflow crowns, a central lumen therethrough, a plurality of first attachment members located at the inflow end, and a plurality of second attachment members disposed at at least a portion of the endmost outflow crowns of the plurality of endmost outflow crowns; and a delivery system for delivery of the prosthetic device to a body lumen, the delivery system including a first shaft including a distal tip attached thereto and an outflow capture device mounted on a distal end thereof, the outflow capture device configured for engagement through openings in the plurality of second attachment members on the prosthetic device;

a second shaft slidingly disposed over the first shaft, wherein the second shaft includes an inflow capture device mounted on a distal end thereof, the inflow capture device configured for engagement through openings in the plurality of first attachment members on the prosthetic device; and a retractable sheath slidingly disposed over the second shaft to hold the prosthetic device in a radially compressed configuration for delivery to a body lumen, wherein the outflow capture device is a coil including a first complete winding and a second complete winding wherein when the prosthetic device is in the radially compressed configuration, each attachment member of the plurality of second attachment members is attached to the coil and the plurality of second attachment members are attached to the first and second complete windings of the coil in a non-consecutive manner, and wherein the outflow capture device includes a polymeric sleeve disposed over an outer surface thereof, the polymeric sleeve being attached to and proximally extending from the distal tip of the first shaft, wherein the polymeric sleeve is formed from a material that is sufficiently soft and flexible to be rolled or flipped.

19. The system of claim 18, wherein the plurality of second attachment members include at least a first set of second attachment members and a second set of second attachment members, and wherein each attachment member of the first set of second attachment members is disposed adjacent to at least one attachment member of the second set of second attachment members, and wherein when the prosthetic device is in the radially compressed configuration, the first complete winding of the coil engages through openings in the first set of second attachment members and the second complete winding of the coil engages through openings in the second set of second attachment members.

* * * * *